US012576208B2

(12) United States Patent
Patek et al.

(10) Patent No.: US 12,576,208 B2
(45) Date of Patent: Mar. 17, 2026

(54) SYSTEM AND METHOD FOR TITRATING BASAL INSULIN DOSES

(71) Applicant: Dexcom, Inc., San Diego, CA (US)

(72) Inventors: Stephen D. Patek, Charlotteville, VA (US); Matthew S. Gerber, San Diego, CA (US); Enrique Campos-Nanez, San Diego, CA (US); Thibault Gautier, San Diego, CA (US); Leah Ziegler, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 510 days.

(21) Appl. No.: 18/139,427

(22) Filed: Apr. 26, 2023

(65) Prior Publication Data

US 2023/0338654 A1 Oct. 26, 2023

Related U.S. Application Data

(60) Provisional application No. 63/335,176, filed on Apr. 26, 2022.

(51) Int. Cl.
*A61M 5/172* (2006.01)
*A61M 5/168* (2006.01)

(52) U.S. Cl.
CPC ...... *A61M 5/1723* (2013.01); *A61M 5/1687 7* (2013.01); *A61M 2202/0486* (2013.01); *A61M 2205/50* (2013.01)

(58) Field of Classification Search
CPC ............ A61M 5/1723; A61M 5/16877; A61M 2202/0486; A61M 2205/50; G16H 50/20; G16H 20/17; G16H 50/50
See application file for complete search history.

(56) References Cited

U.S. PATENT DOCUMENTS

| | | |
|---|---|---|
| 7,766,829 B2 | 8/2010 | Sloan et al. |
| 8,370,077 B2 | 2/2013 | Bashan et al. |
| 8,457,901 B2 | 6/2013 | Beshan et al. |

(Continued)

FOREIGN PATENT DOCUMENTS

| | | |
|---|---|---|
| EP | 1945095 A2 | 7/2008 |
| EP | 2393415 B1 | 11/2015 |

(Continued)

OTHER PUBLICATIONS

Bard R.J., "d-Nav® System 510(k) Summary—K181916", Hygieia, Inc., Feb. 4, 2019, pp. 1-14, Retrieved from the Internet: https://www.accessdata.fda.gov/cdrh_docs/pdf18/K181916.pdf.

(Continued)

*Primary Examiner* — William H Rodriguez

(74) *Attorney, Agent, or Firm* — Klarquist Sparkman, LLP

(57) ABSTRACT

A continuous glucose monitor (CGM)-driven basal insulin titration system and method for patients with Type 2 Diabetes can be adapted to the needs and concerns of subjects just starting on basal insulin therapy. The method uses as inputs historical CGM data, basal insulin dose information, reports of hypoglycemia, and past recommendations and generates an adjusted insulin dose along with a report advising whether to continue the titration process, or to stop. The method can generate a new recommendation on a regular basis (e.g., each day) until it determines an adequate, consistent dose size.

34 Claims, 9 Drawing Sheets

(56) References Cited

U.S. PATENT DOCUMENTS

| | | | |
|---|---|---|---|
| 8,600,682 | B2 | 12/2013 | Bashan et al. |
| 8,690,820 | B2 | 4/2014 | Cinar et al. |
| 9,056,165 | B2 | 6/2015 | Steil et al. |
| 9,669,162 | B2 | 6/2017 | Sloan et al. |
| 9,795,738 | B2 | 10/2017 | Steil et al. |
| 9,833,570 | B2 | 12/2017 | El-Khatib et al. |
| 10,010,291 | B2 | 7/2018 | Budiman et al. |
| 10,137,172 | B2 | 11/2018 | Johansen et al. |
| 10,272,198 | B2 | 4/2019 | Bashan et al. |
| 10,293,109 | B2 | 5/2019 | Bengtsson et al. |
| 10,297,350 | B2 | 5/2019 | Duke et al. |
| 10,332,632 | B2 | 6/2019 | Duke et al. |
| 10,332,633 | B2 | 6/2019 | Duke et al. |
| 10,335,464 | B1 * | 7/2019 | Michelich .............. G16H 40/63 |
| 10,478,100 | B2 | 11/2019 | Tubb |
| 10,722,650 | B2 | 7/2020 | Duke et al. |
| 10,835,671 | B2 | 11/2020 | Desborough et al. |
| 11,017,891 | B2 | 5/2021 | Tubb |
| 11,097,052 | B2 | 8/2021 | Lintereur et al. |
| 11,110,221 | B2 | 9/2021 | Kronenberger |
| 11,147,920 | B2 | 10/2021 | Finan et al. |
| 11,147,921 | B2 | 10/2021 | Desborough et al. |
| 11,166,650 | B2 | 11/2021 | Tubb |
| 11,195,607 | B2 * | 12/2021 | Van Orden ............ G16H 40/63 |
| 11,282,598 | B2 | 3/2022 | Van Orden et al. |
| 11,298,461 | B2 | 4/2022 | Aradottir et al. |
| 11,373,746 | B2 | 6/2022 | Aradottir et al. |
| 11,457,863 | B1 | 10/2022 | Roy et al. |
| 11,511,039 | B2 | 11/2022 | Mazlish et al. |
| 11,872,034 | B2 * | 1/2024 | Escobar ................. G16H 40/67 |
| 2009/0036753 | A1 | 2/2009 | King |
| 2013/0338629 | A1 | 12/2013 | Agrawal et al. |
| 2013/0338630 | A1 | 12/2013 | Agrawal et al. |
| 2016/0082187 | A1 | 3/2016 | Schaible et al. |
| 2016/0256629 | A1 | 9/2016 | Grosman et al. |
| 2017/0266380 | A1 | 9/2017 | Sloan et al. |
| 2019/0272923 | A1 | 9/2019 | Duke et al. |
| 2019/0336683 | A1 | 11/2019 | O'Connor et al. |
| 2019/0336684 | A1 * | 11/2019 | O'Connor .......... A61B 5/14532 |
| 2019/0365995 | A1 | 12/2019 | Bashan et al. |
| 2019/0388512 | A1 | 12/2019 | Michelich et al. |
| 2020/0046268 | A1 | 2/2020 | Patek et al. |
| 2020/0108204 | A1 * | 4/2020 | Mazlish ............ A61M 5/14248 |
| 2020/0227170 | A1 | 7/2020 | Shvets et al. |
| 2020/0275884 | A1 | 9/2020 | Bashan et al. |
| 2021/0060245 | A1 | 3/2021 | Desborough et al. |
| 2021/0193285 | A1 | 6/2021 | Nimri et al. |
| 2021/0260289 | A1 * | 8/2021 | Kamath .............. A61M 5/1723 |
| 2021/0327555 | A1 | 10/2021 | Imanbayev |
| 2021/0361864 | A1 | 11/2021 | Lintereur et al. |
| 2022/0023391 | A1 | 1/2022 | Michelich et al. |
| 2022/0031949 | A1 | 2/2022 | Mazlish et al. |
| 2022/0031950 | A1 | 2/2022 | Finan et al. |
| 2022/0059206 | A1 | 2/2022 | Teucher et al. |
| 2022/0168505 | A1 * | 6/2022 | Li .......................... G16H 20/10 |
| 2022/0184310 | A1 | 6/2022 | Aradottir et al. |
| 2022/0233772 | A1 | 7/2022 | Ulrich et al. |
| 2022/0241503 | A1 | 8/2022 | Zheng et al. |
| 2022/0254472 | A1 | 8/2022 | Dassau et al. |
| 2023/0330335 | A1 * | 10/2023 | Sjolund .................. G16H 40/67 |
| 2024/0058532 | A1 * | 2/2024 | Patek ............... A61M 5/16877 |
| 2024/0188900 | A1 * | 6/2024 | Gouze .................. A61B 5/4839 |
| 2024/0249810 | A1 * | 7/2024 | Patek ...................... G16H 50/50 |
| 2024/0312590 | A1 * | 9/2024 | Totawat ................. G16H 20/17 |
| 2025/0299823 | A1 * | 9/2025 | Vettoretti ............ A61M 5/1723 |
| 2025/0308666 | A1 * | 10/2025 | Bhattacharya ..... A61B 5/14503 |

FOREIGN PATENT DOCUMENTS

| | | | |
|---|---|---|---|
| EP | 3122254 | A1 | 2/2017 |
| EP | 2260423 | B1 | 2/2018 |
| EP | 3374004 | A1 | 9/2018 |
| EP | 2260462 | B1 | 12/2018 |
| EP | 2073870 | B1 | 1/2019 |
| EP | 3453414 | A1 | 3/2019 |
| EP | 3479262 | A1 | 5/2019 |
| EP | 3481274 | A1 | 5/2019 |
| EP | 3030140 | B1 | 6/2019 |
| EP | 3504652 | A1 | 7/2019 |
| EP | 2633456 | B1 | 9/2019 |
| EP | 3549133 | A1 | 10/2019 |
| EP | 3582831 | A1 | 12/2019 |
| EP | 3612255 | A1 | 2/2020 |
| EP | 3639268 | A1 | 4/2020 |
| EP | 2798546 | B1 | 12/2020 |
| EP | 3758008 | A1 | 12/2020 |
| EP | 3465492 | B1 | 3/2021 |
| EP | 3788628 | A1 | 3/2021 |
| EP | 3815106 | A1 | 5/2021 |
| EP | 3254616 | B1 | 6/2021 |
| EP | 3856282 | A1 | 8/2021 |
| EP | 3465491 | B1 | 12/2021 |
| EP | 3998613 | A1 | 5/2022 |
| EP | 3844782 | B1 | 7/2022 |
| WO | 2007056638 | A3 | 11/2007 |
| WO | 2007149533 | A9 | 4/2008 |
| WO | 2008030347 | A8 | 6/2008 |
| WO | 2009146119 | A2 | 12/2009 |
| WO | 2009146119 | A3 | 1/2010 |
| WO | 2010089307 | A1 | 8/2010 |
| WO | 2012058694 | A2 | 5/2012 |
| WO | 2013037754 | A2 | 3/2013 |
| WO | 2013184896 | A1 | 12/2013 |
| WO | 2015021041 | A2 | 2/2015 |
| WO | 2015148930 | A1 | 10/2015 |
| WO | 2016001185 | A1 | 1/2016 |
| WO | 2016048823 | A1 | 3/2016 |
| WO | 2017124006 | A1 | 7/2017 |
| WO | 2017209902 | A1 | 12/2017 |
| WO | 2017209903 | A1 | 12/2017 |
| WO | 2017209904 | A1 | 12/2017 |
| WO | 2018007172 | A1 | 1/2018 |
| WO | 2018037080 | A1 | 3/2018 |
| WO | 2018099912 | A1 | 6/2018 |
| WO | 2018152358 | A1 | 8/2018 |
| WO | 2018194838 | A1 | 10/2018 |
| WO | 2018228932 | A1 | 12/2018 |
| WO | 2019077482 | A1 | 4/2019 |
| WO | 2019213493 | A1 | 11/2019 |
| WO | 2020002428 | A1 | 1/2020 |
| WO | 2020043922 | A1 | 3/2020 |
| WO | 2020068189 | A1 | 4/2020 |
| WO | 2021007391 | A1 | 1/2021 |
| WO | 2022081788 | A1 | 4/2022 |
| WO | 2022164690 | A1 | 8/2022 |
| WO | 2023003800 | A1 | 1/2023 |

OTHER PUBLICATIONS

Bee Y.M., et al., "A Smartphone Application to Deliver a Treat-to-Target Insulin Titration Algorithm in Insulin-Naive Patients With Type 2 Diabetes: A Pilot Randomized Controlled Trial", Diabetes Care, Oct. 1, 2016, vol. 39, No. 10, pp. e174-e176, Retrieved from the Internet: https://diabetesjournals.org/care/article/39/10/e174/120/A-Smartphone-Application-to-Deliver-a-Treat-to.

Berget C., et al., "Clinical Implementation of the Omnipod 5 Automated Insulin Delivery System: Key Considerations for Training and Onboarding People With Diabetes", Clinical Diabetes, Apr. 15, 2022, vol. 40(2), pp. 168-184, Retrieved from the Internet: https://diabetesjournals.org/clinical/article/40/2/168/138902/Clinical-Implementation-of-the-Omnipod-5-Automated.

Bigfoot Biomedical: "Bigfoot Biomedical Acquires Reinforcement Learning Algorithm for Insulin Titration Developed at McGill University", Mar. 30, 2023 [Retrieved on Oct. 29, 2023], pp. 1-3, Retrieved from the Internet: https://www.bigfootbiomedical.com/about/press-room/bigfoot-biomedical-acquires-reinforcement-learning-algorithm-for-insulin-titration-developed-at-mcgill.

Caron S., "Insulin Algorithms System 510(K) Summary—K160673", Insulin Algorithms, Jun. 7, 2017, 7 pages, Retrieved from the Internet: https://www.accessdata.fda.gov/cdrh_docs/pdf16/K160673.pdf.

(56) References Cited

OTHER PUBLICATIONS

Clinicaltrials: "A Study of A Novel Approach to Titrate Basal Insulin (LY2963016) in Participants With Type 2 Diabetes", Aug. 24, 2021 [Retrieved on Oct. 29, 2023], pp. 1-5, Retrieved from the Internet: https://clinicaltrials.gov/study/NCT04864977.

Cooper D.J., et al., "Continuous glucose monitoring reveals similar glycemic variability in individuals with obesity despite increased HOMA-IR", Frontiers in Nutrition, Dec. 2, 2022, vol. 9, pp. 01-09, Retrieved from the Internet: https://www.frontiersin.org/articles/10.3389/fnut.2022.1070187/full.

Cui L., et al., "Inpatient and Outpatient Technologies to Assist in the Management of Insulin Dosing", Clinical Diabetes, Dec. 2020, vol. 38(5), pp. 462-473, Retrieved from the Internet: https://www.ncbi.nlm.nih.gov/pmc/articles/PMC7755045/.

DEN No. DEN170043, "Evaluation of Automatic Class III Designation for DreaMed Advisor Pro", Decision Summary, pp. 1-10, Retrived from the Internet: https://www.accessdata.fda.gov/cdrh_docs/reviews/DEN170043.pdf.

d-nav.com [Online], "d-Nav—A Better Way to Use Insulin", 2023, 3 pages, Retrieved from the Internet: https://d-nav.com/.

DreaMed Diabetes Ltd., "510(k) Substantial Equivalence Determination, 510(k) No. K210561", Decision Summary (Instrument Only), pp. 1-8, Retrived from the Internet: https://www.accessdata.fda.gov/cdrh_docs/reviews/K210561.pdf.

Eberle C., et al., "Real-time State Estimation and Long-term Model Adaptation: a Two-sided Approach toward Personalized Diagnosis of Glucose and Insulin levels", Journal of Diabetes Science and Technology, Sep. 2012, vol. 6(5), pp. 1148-1158. Retrieved from the Internet: https://pubmed.ncbi.nlm.nih.gov/23063042/.

Fathi A.E., et al., "A pilot non-inferiority randomized controlled trial to assess automatic adjustments of insulin doses in adolescents with type 1 diabetes on multiple daily injections therapy", Pediatric Diabetes, Sep. 2020, vol. 21, No. 6, pp. 1-10, Retrieved from the Internet: https://onlinelibrary.wiley.com/doi/10.1111/pedi.13052.

Hansen A.H., et al., "Predicting Plasma Glucose From Interstitial Glucose Observations Using Bayesian Methods", Journal of Diabetes Science and Technology, 2014, vol. 8(2), pp. 321-330. Retrieved from the Internet: https://www.ncbi.nlm.nih.gov/pmc/articles/PMC4455396/.

Hawlas H.J., et al., "Predictive Algorithm for the Insulin Dose Selection with Continuous Glucose Monitoring System", Mechatronics, 2013, pp. 771-777, Retrieved from the Internet: https://link.springer.com/chapter/10.1007/978-3-319-02294-9_97.

Hermanns N., et al., "Evaluation of a Digital Health Tool for Titration of Basal Insulin in People With Type 2 Diabetes: Rationale and Design of a Randomized Controlled Trial", Journal of Diabetes Science and Technology, Jan. 5, 2023, 1 page, Retrieved from the Internet: https://pubmed.ncbi.nlm.nih.gov/36602040/.

Huo Z., et al., "Predicting the Meal Macronutrient Composition from Continuous Glucose Monitors", IEEE EMBS International Conference on Biomedical & Health Informatics (BHI), May 19-22, 2019, 4 pages, Retrieved from the Internet: https://ieeexplore.ieee.org/document/8834488.

insulia.com [Online], "insulia—Helping you get to the right dose. Every day.", 2022 [Retrieved on Oct. 30, 2023], 1 page, Retrieved from the Internet: https://insulia.com/.

International Search Report and Written Opinion for Application No. PCT/US2023/019913, mailed Aug. 18, 2023, 14 pages.

ISage Rx: "Get the Support You Deserve", 2017 [Retrieved on Oct. 30, 2023], pp. 1-2, Retrieved from the Internet: https://isageapp.com.

Janine Freeman R.D., et al., "The Use of Continuous Glucose Monitoring to Evaluate the Glycemic Response to Food", Diabetes spectrum, Apr. 1, 2008, vol. 21(2), pp. 134-137, Retrieved from the Internet: https://diabetesjournals.org/spectrum/article/21/2/134/1997/The-Use-of-Continuous-Glucose-Monitoring-to.

Jemima Jebaseeli T., et al., "Machine Learning and Internet of Things Techniques to Assist the Type I Diabetic Patients to Predict the Regular Optimal Insulin Dosage", Internet of Medical Things, Chapter 9, Apr. 14, 2021, pp. 159-174, Retrieved from the Internet: https://link.springer.com/chapter/10.1007/978-3-030-63937-2_9.

Krikorian R., "Insulia Diabetes Management Companion 510(K) Summary—K161433", Voluntis S.A., Nov. 8, 2016, pp. 1-6, Retrieved from the Internet: https://www.accessdata.fda.gov/cdrh_docs/pdf16/K161433.pdf.

Krishnamoorthy D., et al., "A Model-Free Approach to Automatic Dose Guidance in Long Acting Insulin Treatment of Type 2 Diabetes", IEEE Control Systems Letters, Dec. 2021, vol. 5, No. 6, pp. 2030-2035, Retrieved from the Internet: https://ieeexplore.ieee.org/document/9308924.

Lloyd B., et al., "iDECIDE: A Mobile Application for Insulin Dosing Using an Evidence Based Equation to Account for Patient Preferences", Studies in Health Technology and Informatics, 2015, vol. 216, pp. 1-15, Retrieved from the Internet: https://pubmed.ncbi.nlm.nih.gov/26262017/.

Modulai: "Detecting Food Intake in Glucose Time-Series from Diabetes Patients", AI for Medtech, 2023 [Retrieved on Oct. 30, 2023], pp. 1-4, Retrieved from the Internet: https://modulai.io/case/detecting-food-intake-in-glucose-time-series-from-diabetes-patients/.

Noaro G., et al., "An Ensemble Learning Algorithm Based on Dynamic Voting for Targeting the Optimal Insulin Dosage in Type 1 Diabetes Management", 43rd Annual International Conference of the IEEE Engineering in Medicine & Biology Society (EMBC), 2021, pp. 1828-1831, Retrieved from the Internet: https://ieeexplore.ieee.org/document/9630843.

Pasi T., "Glooko Mobile Insulin Dosing System (MIDS) 510(K) Summary—K171450", Glooko, Inc., Feb. 2, 2018, pp. 1-6, Retrived from the Internet: https://www.accessdata.fda.gov/cdrh_docs/pdf17/K171450.pdf.

Philis-Tsimikas A., et al., "202-OR: Basal Insulin Digital Titration App vs. Enhanced Paper Titration Tool: A Randomized Control Study", Diabetes, Jun. 1, 2020, vol. 69, No. 1, 17 pages, Retrieved from the Internet: https://diabetesjournals.org/diabetes/article/69/Supplement_1/202-OR/57488/202-OR-Basal-Insulin-Digital-Titration-App-vs.

Roy S., "BlueStar® Rx 510(k) Summary—K193654", WellDoc, Inc., Dec. 30, 2019, pp. 1-7, Retrieved from the Internet: https://www.accessdata.fda.gov/cdrh_docs/pdf19/K193654.pdf.

Schiavon M., et al., "Quantitative Estimation of Insulin Sensitivity in Type 1 Diabetic Subjects Wearing a Sensor-Augmented Insulin Pump", Diabetes Care, May 2014, vol. 37, No. 5, pp. 1216-1223, Retrieved from the Internet: https://www.ncbi.nlm.nih.gov/pmc/articles/PMC3994930.

Smith E.J., "Intelligent Dosing System for Insulin-My Insulin Doser 510(k) Premarket Notification and Summary—K082512," Dimensional Dosing Systems, Inc., 2008 [Retrieved on Oct. 29, 2023], 10 pages, Retrieved from the Internet: https://www.accessdata.fda.gov/scripts/cdrh/cfdocs/cfPMN/pmn.cfm?ID=K082512.

Sun Q., et al., "A Dual Mode Adaptive Basal-Bolus Advisor Based on Reinforcement Learning", IEEE Journal of Biomedical and Health Informatics, Dec. 16, 2018, vol. 23(6), pp. 1-9, Retrieved from the Internet: https://ieeexplore.ieee.org/document/8579186.

Sysko R., "iSage Rx (iSage Rx Basal Insulin Titration)", Indications for Use, Mar. 7, 2017, 3 pages, Retrived from the Internet: https://www.accessdata.fda.gov/cdrh_docs/pdf16/K161865.pdf.

Tamez-Pérez H.E., et al., "Effect of Digital-Tool-Supported Basal Insulin Titration Algorithm in Reaching Glycemic Control in Patients with Type 2 Diabetes in Mexico", Journal of Diabetes Science and Technology, Nov. 2022, vol. 16, No. 6, pp. 1-8, Retrieved from the Internet: https://pubmed.ncbi.nlm.nih.gov/34323110/.

Tyler N.S., et al., "Artificial Intelligence in Decision Support Systems for Type 1 Diabetes", Sensors, Jun. 5, 2020, vol. 20(11), pp. 1-26, Retrieved from the Internet: https://www.mdpi.com/1424-8220/20/11/3214.

Waldenmaier D., et al., "Suitability of Continuous Glucose Monitoring in Healthy Subjects to Detect Effects of Meal Sequences and Nutritional Content of Meals on Postprandial Glycemic Responses", Research Square, Sep. 28, 2022, pp. 1-19, Retrieved from the Internet: https://europepmc.org/article/ppr/ppr551763.

WELLDOC: "Welldoc Receives FDA Clearance for Long-Acting Insulin Support for Award-Winning Digital Health Solution BlueStar®",

(56) References Cited

OTHER PUBLICATIONS

Jun. 3, 2020 [Retrieved on Oct. 29, 2023], pp. 1-2, Retrieved from the Internet: https://www.welldoc.com/news/fda-clearance-long-acting-insulin-support-bluestar/.

Zheng M., et al., "Automated Meal Detection from Continuous Glucose Monitor Data through Simulation and Explanation", Journal of the American Medical Informatics Association, Sep. 27, 2019, vol. 26(12), pp. 1592-1599. Retrieved from the Internet: https://pubmed.ncbi.nlm.nih.gov/31562509/.

Inzucchi S.E., et al., "Management of Hyperglycemia in Type 2 Diabetes: A Patient-Centered Approach: Position Statement of the American Diabetes Association (ADA) and the European Association for the Study of Diabetes (EASD)," Diabetes Care, Jun. 2012, vol. 35, pp. 1364-1379.

Lasalle J.R., et al., "Insulin Therapy in Type 2 Diabetes Mellitus: A Practical Approach for Primary Care Physicians and Other Health Care Professionals," The Journal of the American Osteopathic Association, Feb. 2013, vol. 113, No. 02, pp. 152-163.

Shubrook J.H., "Insulin for Type 2 Diabetes: How and When to Get Started," The Journal of Family Practice, Feb. 2014, vol. 63, No. 02, pp. 76-81.

* cited by examiner

SYSTEM AND METHOD FOR TITRATING BASAL INSULIN DOSES

CROSS REFERENCE TO RELATED APPLICATION

This application claims the benefit of U.S. Provisional Application Ser. No. 63/335,176, filed Apr. 26, 2022, the contents of which are incorporated herein by reference.

BACKGROUND

Long-acting (basal) insulin therapy for patients with Type 2 Diabetes can be an intimidating process for both patients and their caregivers. Insulin may be the first patient-injected pharmaceutical for some patients, and this can cause fear and discomfort. The titration process traditionally also involves daily finger-stick measurements of fasting blood glucose (BG), causing additional discomfort. Finally, and importantly, insulin comes with a risk of hypoglycemia, which causes some to fear this necessary and helpful therapy.

Clinically, providers must rely on patient compliance with finger-stick BG measurements to guide them through the insulin titration process. Providers also rely on patients to self-report hypoglycemia. Analysis of data from observational studies indicate that some patients on basal insulin therapy may be experiencing significant amounts of time in hypoglycemia. Patients' inadequate self-monitoring and/or reporting of hypoglycemic events may also be a barrier in finding the appropriate insulin dosage.

Conceptually, incorporation of continuous glucose monitoring CGM could address several unmet needs in the standard process of initiating insulin in treatment of Type 2 Diabetes. CGM provides robust and comprehensive glucose control metrics, which can be coupled with computational techniques to recommend a titration path that is faster and safer. CGM-based basal insulin titration also has the potential to reduce burden on health care providers through automated, patient-facing deployments.

CGM-based automated basal insulin titration improves upon conventional manual titration based on Self-Monitoring of Blood Glucose (SMBG) in several ways. As opposed to relying on one, or just a few, finger-stick samples, CGM provides a holistic view of the patient's blood glucose variation throughout the day, accurately characterizing the patient's exposure to both hypo- and hyperglycemia. Conventional titration relies on the assumption that the patient will sample blood glucose when in a fasting state, which cannot be verified independently, and this results in several potential hazards: (i) the patient's actual fasting blood glucose level can be lower than the sample values obtained by the patient, (ii) the patient's lowest blood glucose of the day (achieved at a different time of the day) could be significantly lower than the sample values obtained by the patient, and (iii) the misleading samples collected by the patient cause the conventional titration procedure to settle on an artificially high basal insulin dose, exposing the patient to unnecessary risk of hypoglycemia. By not relying on a single, patient-declared fasting blood sample each day, the CGM-based automated basal insulin titration can avoid all these hazards. In addition, CGM provides information about the nature of the patient's exposure to hyperglycemia, e.g. whether it is (i) persistent throughout the day (where increasing the patient's basal dose is an obvious choice) or (ii) fluctuating between extremes (where increasing the patient's dose must be carefully considered). Indeed, if the patient is already experiencing both significant hyperglycemia (measured for example by A1c, mean glucose, or time-above-range) and also appreciable hypoglycemia (measured for example by the number, duration, or depth of low blood glucose events), then adjusting the patient's basal insulin may produce only marginal benefit, and it may be advisable for the patient/HCP to consider other more significant modifications to therapy, e.g. the addition of prandial (rapid-acting) insulin at one or more meals per day. CGM provides a sufficiently rich signal to tease apart these various considerations, and automation removes subjectivity from the analysis of the data. With a clear view to the statistical nature of the patient's blood glucose variability, CGM-based automated insulin titration has the potential to arrive at a final, safer and more effective dose than the conventional method, and can reach this conclusion faster than with SMBG-based manual basal insulin titration. From a human factors perspective, CGM-based automated basal insulin titration minimizes the opportunity for user error, e.g. in not requiring the patient to manually log SMBG samples or to manually compute dose changes. In addition, if the patient is using a connected or "smart" insulin pen, then the patient would not even have to log/report basal insulin doses.

SUMMARY

In a first aspect, a basal titration adjustment device is presented for titrating a basal insulin dose for a subject. The device includes one or more processors, a continuous glucose monitor (CGM) module, an insulin module, at least a first dose-daily blood glucose state response modeler, a target dose adjuster and a dose finalizer. The CGM module, when executed by the one or more processors, receives CGM data obtained over at least a series of days and generates historical estimated glucose values (EGVs) therefrom and further generates from the EGVs values for each of a plurality of daily blood glucose state parameters each reflective of an aspect of a blood glucose state of the subject. The insulin module, when executed by the one or more processors, receives daily basal insulin dose values administered to the subject over the series of days and generates therefrom daily effective doses that each represent a total plasma insulin serving the subject for that respective day and account for an accumulation of insulin in the subject from all previously administered doses. The first dose-daily blood glucose state response modeler, when executed by the one or more processors, receives a first of the plurality of daily blood glucose state parameters and the daily effective doses and generates therefrom a first regularized dose-response model relating the first daily blood glucose state parameter to an effective basal insulin dose. The target dose adjuster, when executed by the one or more processors, receives the first regularized dose-response model and generates therefrom a target basal insulin dose that is to produce a value of the first daily blood glucose state parameter that is predicted by the first regularized dose-response model with at least a specified confidence level. The dose finalizer, when executed by the one or more processors, receives the target basal insulin dose and values of one or more of the daily blood glucose state parameters and produces therefrom an adjusted basal insulin dose that modifies the target basal insulin dose in conformance with one or more pre-established safety rules.

In an embodiment of the first aspect, the plurality of daily blood glucose state parameters are selected from the group consisting of an effective fasting blood glucose (EFBG)

parameter, a low blood glucose risk parameter representing a daily risk of experiencing a low EGV, a low daily EGV parameter specifying whether or not the subject experienced an EGV below a specified level on a given day and a daily reference blood glucose parameter reflecting a comparison of a daily EGV to a therapeutic target EGV.

In an embodiment of the first aspect, the first regularized dose-response model is a regularized linear regression model.

In an embodiment of the first aspect, the first regularized dose-response model is regularized using population data to bias at least an initial target dose to a safe dose at a population level.

In an embodiment of the first aspect, the first daily blood glucose state parameter is a daily estimated fasting blood glucose (EFBG) parameter.

In an embodiment of the first, the first daily blood glucose state parameter is a low blood glucose risk parameter.

In an embodiment of the first aspect, the one or more pre-established safety rules reduce a risk of hypoglycemia.

In an embodiment of the first aspect, the basal titration adjustment device further includes a reported hypoglycemia module that, when executed by the one or more processors, receives hypoglycemic event data reported by the subject and generates a hypoglycemic report history from the hypo- glycemic event data and the historical EGVs, the hypogly- cemic report history specifying a time and severity of credible hypoglycemic events reported by the subject, wherein the dose finalizer, when executed by the one or more processors, produces the adjusted basal insulin dose using the hypoglycemic report history as an additional input.

In an embodiment of the first aspect, the basal titration adjustment device further includes a termination checker module that, when executed by the one or more processors, receives values of some or all of the plurality of daily blood glucose state parameters, the hypoglycemic report history and adjusted basal insulin doses produced on previous days and generates therefrom a termination report indicating whether titration of basal insulin should terminate or con- tinue.

In an embodiment of the first aspect, the at least a first dose-daily blood glucose state response modeler includes a second dose-daily blood glucose state response modeler that, when executed by the one or more processors, receives a second of the plurality of daily blood glucose state parameters and the daily effective doses and generates therefrom a second regularized dose-response model relat- ing the second daily blood glucose state parameter to an effective basal insulin dose, the target dose adjuster, when executed by the one or more processors, receives the first and second regularized dose-response models and generates therefrom the target basal insulin dose.

In an embodiment of the first aspect, the first daily blood glucose state parameter is a daily estimated fasting blood glucose parameter and the second daily blood glucose state parameter is a low blood glucose risk parameter specifying a risk that the subject has an EGV below a threshold at one or more times during a day.

In an embodiment of the first aspect, the first regularized linear-regression model includes values for a slope, intercept and a measure of uncertainty.

In an embodiment of the first aspect, values of the EFBG parameter are based on CGM data obtained at a specified time of day.

In an embodiment of the first aspect, values of the EFBG parameter are based on CGM values that are below a certain percentile of a blood glucose distribution of the subject.

In an embodiment of the first aspect, a hypoglycemic event is treated as not relevant if it occurred more than a specified period of time before a current time or if it occurred when a then-current adjusted basal insulin dose is different from a current adjusted basal insulin dose by more than a specified amount.

In an embodiment of the first aspect, the first dose-daily blood glucose state response modeler produces a basal insulin dose-low blood glucose risk regression model that predicts a low blood glucose risk corresponding to an effective basal insulin dose.

In an embodiment of the first aspect, the basal insulin dose-low blood glucose risk regression model is a linear regularized linear regression model.

In an embodiment of the first aspect, the linear regularized linear regression model is regularized using population data to bias at least an initial target dose to a safe dose at a population level.

In an embodiment of the first aspect, the low blood glucose risk parameter represents a risk that the subject has an EGV below a threshold at one or more times during a day.

In an embodiment of the first aspect, the low blood glucose risk parameter represents a daily EGV that is below a specified percentile of all EGVs for the subject during a day.

In an embodiment of the first aspect, the dose finalizer, when executed by the one or more processors, produces the adjusted basal insulin dose on a periodic basis.

In an embodiment of the first aspect, the periodic basis is a daily basis.

In an embodiment of the first aspect, the target dose adjuster, when executed by the one or more processors, determines a first preliminary target dose from the first regularized dose-response model and a second preliminary target dose from the second regularized dose-response model and produces the target dose by balancing the first preliminary target dose with the second preliminary target dose.

In an embodiment of the first aspect, the target dose that is produced is a minimum of the first and second preliminary target doses, a maximum of the first and second preliminary target doses, or a weighted average of the first and second preliminary target doses.

In an embodiment of the first aspect, the one or more preestablished safety rules prevent a value of a newly generated adjusted basal insulin dose from exceeding a previously generated adjusted basal insulin dose for a pre- vious day.

In an embodiment of the first aspect, the one or more preestablished safety rules establish a value for a design parameter defining a target deadband of EGVs surrounding a target EGV such that a newly generated adjusted basal insulin dose will not be adjusted from a previously generated adjusted basal insulin dose for a value of a daily reference blood glucose parameter within the target deadband.

In an embodiment of the first aspect, the one or more preestablished safety rules generates a warning that over- basalization is predicted to occur.

In an embodiment of the first aspect, the one or more preestablished safety rules constrains modification of the target basal insulin dose if overbasalization is predicted to occur.

In an embodiment of the first aspect, the termination report indicates that titration of the basal insulin dose should terminate if a target value for a daily reference blood glucose parameter cannot be reached without introducing prandial insulin, the daily reference blood glucose parameter reflecting a comparison of a daily EGV to a therapeutic target EGV.

In a second aspect, a method is presented for titrating a basal insulin dose for a subject. The method includes: receiving CGM data obtained over at least a series of days and generating historical estimated glucose values (EGVs) therefrom; generating from the EGVs values for each of a plurality of blood glucose state parameters each reflective of an aspect of a blood glucose state of the subject; receiving basal insulin dose values administered to the subject over the series of days and generates therefrom effective doses that each represent a total plasma insulin serving the subject for that respective day and account for an accumulation of insulin in the subject from all previously administered doses; receiving a first of the plurality of blood glucose state parameters and the effective doses and generating therefrom a first regularized dose-response model relating the first blood glucose state parameter to an effective basal insulin dose; receiving the first regularized dose-response model and generating therefrom a target basal insulin dose that is to produce a value of the first blood glucose state parameter that is predicted by the first regularized dose-response model with at least a specified confidence level; and receiving the target basal insulin dose and values of one or more of the plurality of blood glucose state parameters and producing therefrom an adjusted basal insulin dose that modifies the target basal insulin dose in conformance with one or more pre-established safety rules.

In an embodiment of the second aspect, the basal insulin doses are administered on a daily basis.

In an embodiment of the second aspect, an adjusted basal insulin dose is produced on a daily basis.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure.

DETAILED DESCRIPTION

Described herein is a CGM-driven basal insulin titration system and method for patients with Type 2 Diabetes. The system and method can be adapted to the needs and concerns of subjects just starting on basal insulin therapy. As explained in more detail below, the method uses an inputs historical CGM, basal insulin dose information, reports of hypoglycemia, and past recommendations and generates an adjusted insulin dose along with a report advising whether to continue the titration process, or to stop. The method can generate a new recommendation on a regular basis (e.g., each day) until it determines an adequate, consistent dose size. Some of the illustrative features and advantages of the system and method are as follows.

The system and method can make individualized, model-based dose recommendations by estimating personalized dose-response models from CGM-derived glucose control metrics including glucose value percentiles and estimated fasting glucose. Regularization is added to the personalized model to bias fits in the first few days toward safe recommendations, when the CGM history is still sparse. CGM-based estimates of glucose variability are incorporated into the algorithm design to guard against dose sizes that may increase hypoglycemic risk. Finally, the system accounts for the time-delayed response of long-acting insulin, referred to herein as an insulin Effective Dose. The Effective Dose model is population-based (not personalized).

The system and method also incorporate checks that ensure safe and meaningful dose recommendations. For instance, one check may ensure that the dose does not increase following recent non-severe hypoglycemia. The system can issue an alert when clinical guidelines indicate that a maximum per-kilogram dose has been reached. Additionally, a reference glucose $BG_{ref}$ is estimated each day, and dose changes are forced to be coherent with the estimated value relative to a target value (e.g., dose decreases are not permitted when $BG_{ref}$ is above a target range, and dose increases are not permitted when $BG_{ref}$ is below a target range). The system may also force dose reductions in the presence of CGM-detected and patient-reported severe hypoglycemia.

System Overview

Figure 1:
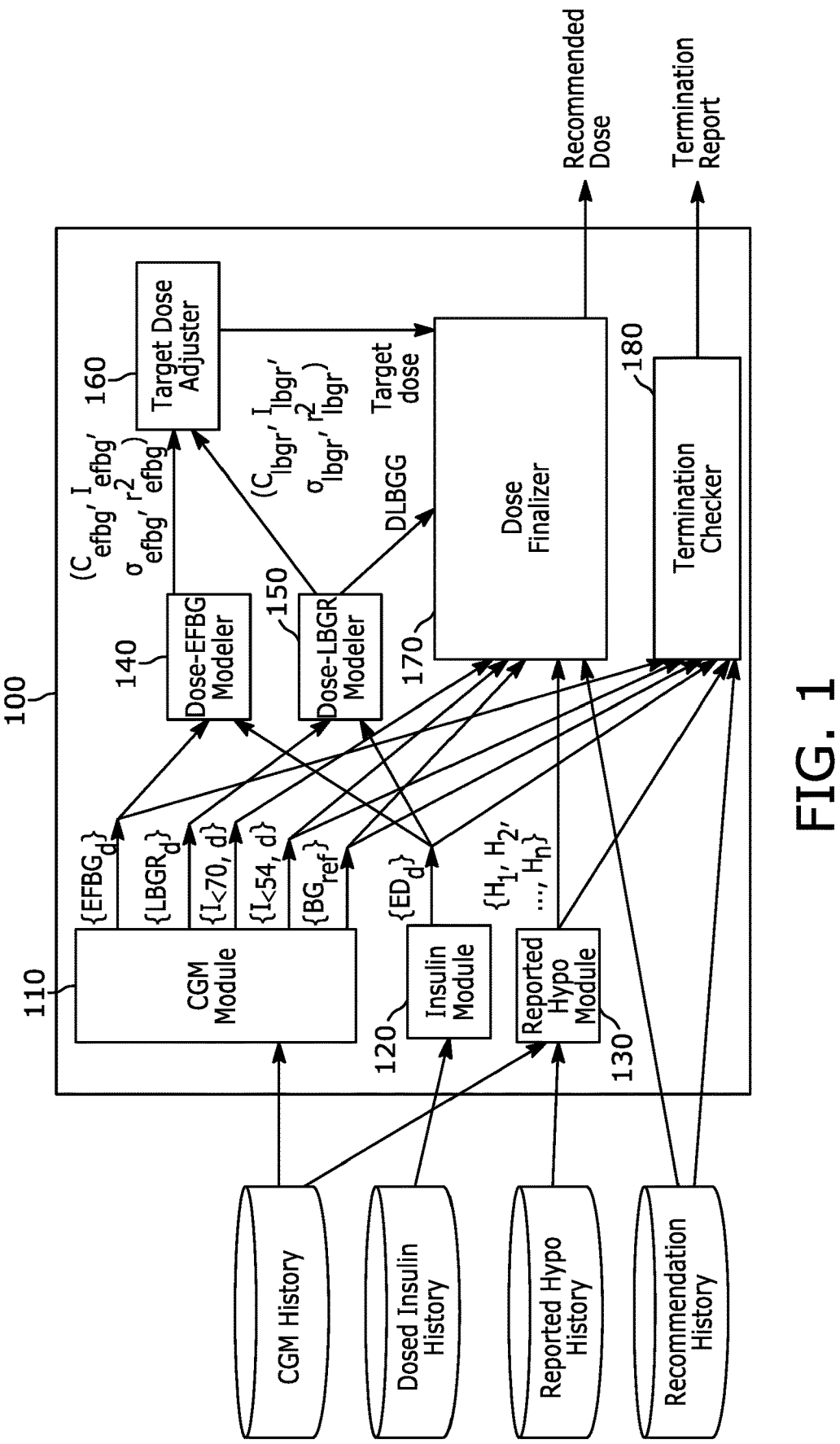
FIG. 1 is a functional block diagram of one example of a basal insulin titration system.

FIG. 1 is a functional block diagram of one example of the basal insulin titration system 100 described herein. As a general matter, the system serves to read in historical data including CGM History, Dosed Insulin History, Reported Hypoglycemia (Hypo) History, and a Recommendation History, and produces both an Adjusted Dose and a Termination Report. CGM history refers to estimated glucose values with timestamps collected since the beginning of the titration process. Dosed Insulin History refers to dosed basal (long-acting) insulin injections with timestamps indicating when administered (e.g., injected) since the beginning of the titration process. Reported Hypo History refers to reported experiences of symptomatic hypoglycemic as reported by the patient, a health care practitioner (HCP), an informal care provider, and/or other concerned individuals, with each report indicating the level of severity of the event. Recommendation History refers to the history of previous adjusted dose amounts during the titration process.

Viewed at a high level, the system operates to (i) interpret CGM History and Dose Insulin History data in the form of one or more dose-response models from which a Target dose is derived and (ii) to account for daily fasting blood glucose values, exposure to hypoglycemia, and past recommendations to compute an Adjusted Dose and to recommend next steps in the form of a Termination Report.

The flow of data through the various components or modules of the system is as follows.

Referring to FIG. 1, CGM History data are read into a CGM Module 110 (see the CGM Module section below), which outputs sequences of (i) daily Estimated Fasting Blood Glucose (EFBG), $\{EFBG_d\}_{d=1, \ldots, t}$, where d=1 corresponds to the first day of the titration process and d=t corresponds to the EFBG value for the current day, (ii) daily Low Blood Glucose Risk (LBGR), $\{LBGR_d\}_{d=1, \ldots, t}$, (iii) daily indicators of non-severe low blood glucose (e.g. less than 70 mg/dl), $\{I_{<70, d}\}_{d=1, \ldots, t}$, where $I_d$=True means that there was an experience of non-severe low blood glucose on day d, (iv) daily indicators of severe low blood glucose (e.g. less than 54 mg/dl), $\{I_{<54, d}\}_{d=1, \ldots, t}$, where $I_d$=True means that there was an experience of severe low blood glucose on day d, and (v) a reference blood glucose value, $BG_{ref}$, the glucose statistic used by the Dose Finalizer to produce the Adjusted Dose.

Dosed Insulin History data are read into an Insulin Module 120 (see the Insulin Module section below), which produces a sequence of Effective Doses (ED), $\{ED_d\}_{d=1, \ldots, t-1}$, where t−1 corresponds to the most recent effective dose—the one that was active during the day of the patient's life measured by CGM and rendered as $EFBG_t$, $LBGR_t$, $I_{<70, t}$, $I_{<54, t}$, and $BG_{ref}$.

Reported Hypo History and CGM History data are read into a Reported Hypo Module 130 (see the Reported Hypo Module section below), which produces a sequence of daily report hypoglycemic flags, $\{H_d\}_{d=1, \ldots, t}$, where $H_d$ takes different values depending on whether severe or non-severe hypo symptomatic hypoglycemia where reported by the patient or caregivers on day d.

Daily Estimated Fasting Blood Glucose data $\{EFBG_d\}_{d=1, \ldots, t}$ and Effective Dose data $\{ED_d\}_{d=1, \ldots, t}$, are read into a Dose-EFBG Modeler 140 (see the Dose-EFBG Modeler section below) that estimates the ED-to-EFBG response. In one implementation of the system, the dose response is approximated as a linear relationship with slope $C_{efbg}$, intercept $I_{efbg}$, residual standard deviation $s_{efbg}$, and quality-of-fit $r^2_{efbg}$.

Daily Low Blood Glucose Risk data $\{LBGR_d\}_{d=1, \ldots, t}$ and Effective Dose data $\{ED_d\}_{d=1, \ldots, t-1}$, are read into a Dose-LBGR Modeler 150 (see the Dose-EFBG Modeler section below) that estimates the ED-to-LBGR response. In one implementation of the system, the dose response is approximated as a linear relationship with slope $C_{lbgr}$, intercept $I_{lbgr}$, residual standard deviation $s_{lbgr}$, and quality-of-fit $r^2_{lbgr}$.

The models produced by the Dose-EFBG Modeler 140 and Dose-LBGR Modeler 150 are read into a Target Dose Adjuster 160 (see the Target Dose Adjuster section below) that produces an adjusted Target dose that balances the desire for fasting glucose in a target range with low blood glucose risk.

An Adjusted Dose is produced by a Dose Finalizer 170 (see the Dose Finalizer section below), which operates on the Target dose (from the Target Dose Adjuster 160) along with (i) the reference glucose $BG_{ref}$, (ii) the indicators of non-severe hypoglycemia $\{I_{<70, d}\}_{d=1, \ldots, t}$ and severe hypoglycemia $\{I_{<54, d}\}_{d=1, \ldots, t}$, (iii) daily reported hypoglycemia $\{H_d\}_{d=1, \ldots, t}$, (iv) past dose recommendations as recorded in the Recommendation History, and possibly (v)

other algorithm status parameters from previous titration recommendations. The Dose Finalizer 170 imposes constraints that ensure that the final Adjusted Dose is safe and matches the patient's expectations based on its experience with blood glucose in the preceding day.

Finally, the outputs of the CGM, Insulin, and Reported Hypo Modules, along with the Recommendation History, are read into a Termination Checker 180 (see the Termination Checker section below), producing a Termination Report articulating whether the titration process should terminate or continue and also making other follow-on recommendations, e.g. when appropriate, suggesting that prandial (rapid-acting) insulin should be added to the patient's therapy regime.

In summary, the basal insulin titration system described herein reads in CGM History, Dose Insulin History, Reported Hypo History, and the Recommendation History e.g., each day, to produce a Dose Recommendation and a Termination Report.

A few alternative embodiments of the high-level system shown in FIG. 1 will now be described.

For example, different implementations may handle historical data in different ways. For instance, in some cases whole histories can be input to the system each day or, alternatively, just differential inputs describing new data since the last recommendation can be input, with most of the history expressed as an evolving "state" of system. Likewise, CGM data can be obtained in different ways, such as by reading the CGM data directly from a CGM device or obtaining it from a database query from a server. Similarly, dosed insulin data can be obtained in different ways such as by reading it in from a smart pen device. Alternatively, dosed insulin data can read in from patient/caregiver-reported doses in a smartphone or web application ("app"). Different implementations of the system can also be used to titrate different types of basal (long-acting) insulin. For instance, the basal insulin being titrated could be insulin glargine. Alternatively, the basal insulin could be other formulations included ones with longer pharmacokinetic profiles (e.g. insulin degludec, insulin icodec) or with shorter pharmacokinetic profiles (e.g. NPH).

The Reported Hypo data can be obtained from patients and/or caregivers in different ways. For example, reported hypo events can be obtained from data collected in a smartphone "app" or it could be collected via a web "app" or "portal". Adjusted dose data can be stored in different ways such as in a smartphone "app" or in a database accessible via a data network.

The titration method described herein can be productized in different ways. For instance, the method could be implemented in different places. For example, Adjusted Dose values and Termination Reports could be computed by a server having access to the CGM, Dosed Insulin, Reported Hypo, and Recommendation Histories. Alternatively, Adjusted Dose values and Termination Reports could be computed by a smart phone or other portable device having access to the CGM, Dosed Insulin, Reported Hypo, and Recommendation Histories. Similarly, the method could be implemented at different times, such as on demand, or it can be pre-computed and transmitted to patients and/or caregivers on a scheduled basis. An example of an environment in which the titration method may be implemented will be described below in connection with FIG. 10.

The output provided by the system and method can also be provided to different parties. For instance, Adjusted Dose values and Termination Reports could be viewed directly and implemented by patients, with caregivers having the ability to monitor therapy remotely. Alternatively, Adjusted Dose values and Termination Reports could be made available first to caregivers (HCPs, GPs, CDEs), who have the ability to approve or reject recommendations before they are sent to their patients.

The termination checker 180 can use different criteria for termination. For instance, the algorithm may be configured to minimize the time required to either reach an optimal abstract daily dose or reach a conclusion that basal insulin alone is insufficient to meet the patient's needs. Alternatively, the termination checker 180 may be configured to run in an ongoing fashion, continuously adapting the patient's insulin dose in response to slowly changing insulin needs, and terminating only when it reaches the conclusion that basal insulin alone is insufficient to meet the patient's needs.

The particular outputs from the CGM Module 110, referred to herein generally as daily blood glucose state parameters may differ in different implementations and can be determined in a variety of different ways. For instance, the Low Blood Glucose Risk (LBGR) can be quantified in different ways (see the CGM Module section below). In illustrative examples, the LBGR can be quantified as a percent time below a threshold glucose level, e.g. percent time below 70 mg/dl (or 3.9 mmol/l), or it can be quantified as the glucose level (in mg/dl or ml/l or other ways) associated with the Xth percentile of daily CGM values, where X could include 0.5, 1, 2, 10, or other percentiles. In other examples the LBGR can be computed as a risk space value as described in U.S. Pat. No. 11,355,238, as a Low Blood Glucose Index (LBGI) or as described in U.S. Pat. No. 9,317,657. Alternatively, the LBGR can be computed as an actionable low blood glucose risk value as described in U.S. Patent Publ. No. 20200178905A1.

The reference blood glucose ($BG_{ref}$), which is another of the daily blood glucose state parameters, also can be quantified in different ways (see the CGM Module section below). For instance, the $BG_{ref}$ can be quantified as the Estimated Fasting Blood Glucose (EFBG) referred to above or as time-average BG computed from CGM, or any other BG statistic that characterizes the overall quality of glycemic control.

In some cases the computation of the Target dose may use different dose response models (see the Target Dose Adjuster section below). For instance, the target dose could be computed using just the Dose-LBGR Modeler, without the Dose-EFBG Modeler, or vice versa. In other embodiments different dose-response models could be used, including nonlinear dose-response models and dose response models that characterize model uncertainty in different ways (other than residual standard deviation and quality-of-fit).

The systems and methods described herein can be adapted to different titration scenarios without changing its basic structure. For example, if the patient is new to basal insulin (either having never used it before or not currently using it), then the parameters of the titrator can be configured to (i) learn dose responses more rapidly and from lower initial doses than would otherwise be the case, (ii) be particularly avoiding of hypoglycemia which is often a concern of new insulin users, and (iii) be appropriately circumspect about reaching the conclusion that basal adjustments alone are insufficient. On the other hand, if the patient is already on basal insulin and is seeking to identify a better daily dose, then the titrator can take advantage of previously available blood glucose and insulin dosing data, and the parameters of the algorithm can be adapted to (i) appropriately learn dose responses near the patient's currently prescribed dose, (ii) be somewhat less concerned about hypoglycemia (since insulin is by now a routine for the patient), and (iii) may more aggressively explore the conclusion that basal-insulin by itself is no longer adequate. In other embodiments, the titrator may be configured for continuous ongoing adaptation of the patient's basal insulin dose, tracking the patient's ever-changing need for basal insulin in response to (i) seasonal effects, (ii) changes in diet/lifestyle, and (iii) changes in underlying physiology.

Illustrative embodiments of the individual components and modules shown in FIG. 1 and some alternatives thereto will be described in more detail below.

CGM Module

Figure 2:
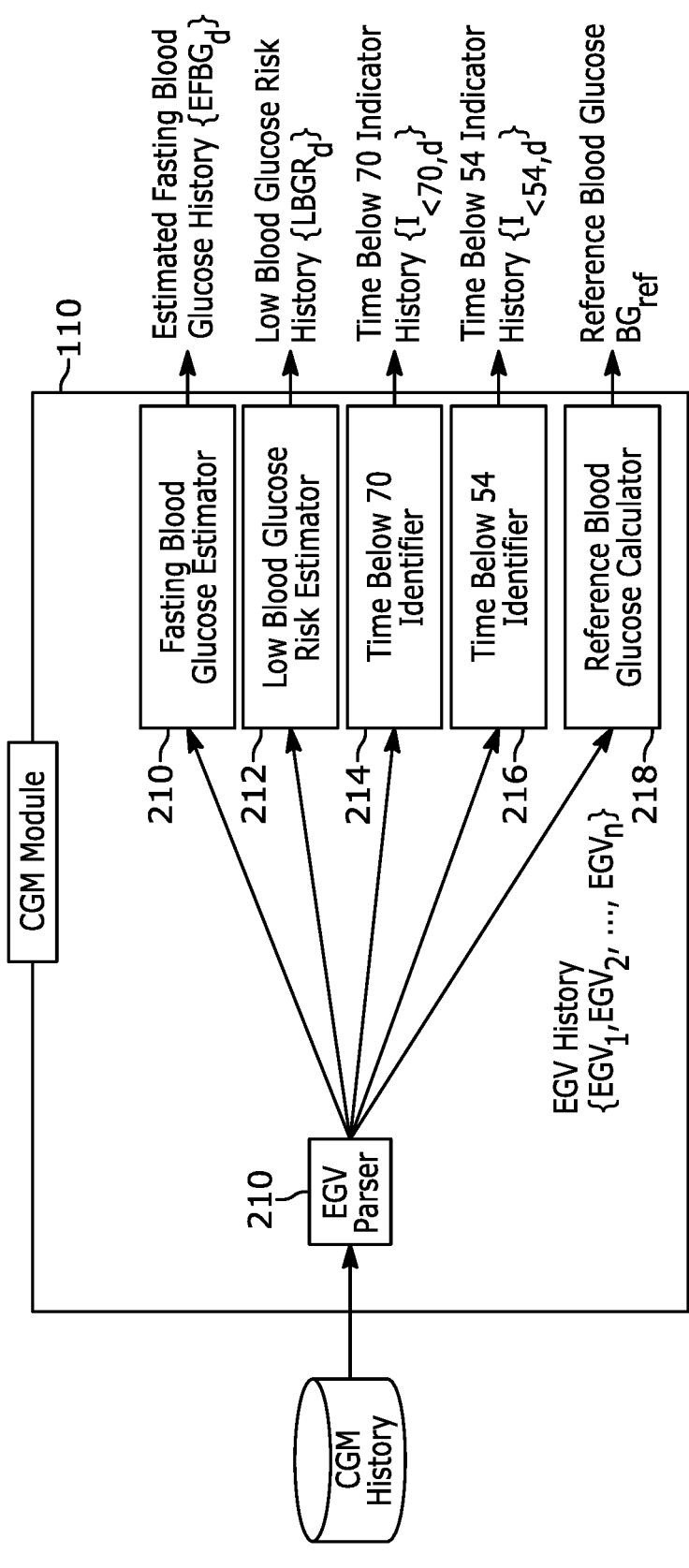
FIG. 2 shows one example of the CGM Module shown in FIG. 1.

As illustrated in FIG. 2, the CGM Module 110 reads in the CGM History and then renders values for a series of daily blood glucose state parameters. In one specific embodiment described herein, values for five such parameters are output:

1. $\{EFBG_d\}$: Estimated Fasting Blood Glucose (EFBG) History, a sequence with one positive numerical value per day d.
2. $\{LBGR_d\}$: Low Blood Glucose Risk (LBGR) History, a sequence with one nonnegative value per day d.
3. $\{I_{<70,d}\}$: Time Below 70 Indicator History, a sequence with one True or False value per day d indicating that the patient did (True) or did not (False) spend a substantial fraction of day d with their blood glucose below 70 mg/dL.
4. $\{I_{<54,d}\}$: Time Below 54 Indicator History, a sequence with one True or False value per day d indicating that the patient did (True) or did not (False) spend a substantial fraction of day d with their blood glucose below 54 mg/dL.
5. $\{BG_{ref}\}$: Reference Blood Glucose value, which drives the Adjusted Dose toward one that achieves $BG_{ref}$ in a specified target range.

As shown in FIG. 2, the CGM Module 110 contains an EGV Parser 200 that reads the CGM History and produces an EGV History $\{EGV_1, EGV_2, \ldots, EGV_n\}$. Each element $EGV_i$ of the EGV History comprises a timestamp and an estimated blood glucose value (mg/dL). The elements of EGV History are ordered by timestamp and nonduplicative with each other. The EGV History is provided as input to each of the CGM Module's five submodules, which correspond to the five outputs. The main steps performed by each submodule are described below.

The Fasting Blood Glucose Estimator 210 (outputs $\{EFBG_d\}$) uses the EGV History to estimate the patient's Fasting Blood Glucose for each day. The Fasting Blood Glucose corresponds to a physiological state that is free of short-term glucose disturbances caused by meals, exercise, illness, and other events. This physiological state is intended to be similar to the state created by a standard fast prior to laboratory blood work. The $EFBG_d$ value is intended to reflect the therapeutic effect of prior Adjusted Doses. Large prior Adjusted Doses are associated with smaller $EFBG_d$ values relative to small prior Adjusted Doses.

The Low Blood Glucose Risk Estimator 212 (outputs $\{LBGR_d\}$) uses the EGV History to estimate the patient's Low Blood Glucose Risk for each day. A high (versus low) $LBGR_d$ value indicates that a confluence factors (e.g., insulin sensitivity, meals and exercise, and doses of basal insulin and/or other medications) caused the patient to experience elevated risks from low blood glucose (e.g., hypoglycemia) on day d.

The Time Below 70 Identifier 214 (outputs $\{I_{<70,d}\}$) uses the EGV History to identify whether the patient spent a substantial fraction of day d with their blood glucose below 70 mg/dL. A single $EGV_i$ below 70 mg/dL could be the result of transient CGM error, or it might be so isolated as to be therapeutically irrelevant. The Time Below 70 Identifier isolates therapeutically relevant $EGV_i$ values below 70 mg/dL, and it flags the corresponding days with True values of $I_{<70,d}$. All other days receive False values for $I_{<70,d}$.

The Time Below 54 Identifier 216 (outputs $\{I_{<54,d}\}$) uses the EGV History to identify whether the patient spent a substantial fraction of day d with their blood glucose below 54 mg/dL. A single $EGV_i$ below 54 mg/dL could be the result of transient CGM error, or it might be so isolated as to be therapeutically irrelevant. The Time Below 54 Identifier isolates therapeutically relevant $EGV_i$ values below 54 mg/dL, and it flags the corresponding days with True values of $I_{<54,d}$. All other days receive False values for $I_{<54,d}$.

The Reference Blood Glucose Calculator 218 (outputs $BG_{ref}$) uses the EGV History to calculate a Reference Blood Glucose value. This reference value characterizes the quality of prior Adjusted Doses vis-a-vis a therapeutic target. A Reference Blood Glucose value above the therapeutic target on day d suggests that the Adjusted Dose might need to increase for day d+1 (see Dose Finalizer for details).

Some alternative implementations of the various submodules of the CGM Module 110 are described below.

In some cases, the Fasting Blood Glucose Estimator 210 may output $\{EFBG_d\}$ as:

a. A statistic of the EGV History for day d with respect to the patient's particular circadian rhythm of sleeping and eating. For example, $EFBG_d$ might be the average $EGV_i$ around the time the patient awakes on day d and prior to their first meal of the day.

b. A statistic of the EGV History for day d that is a specified percentile known to correlate with the physiological state of fasting.

c. An estimation that combines several statistics (e.g., 1a and 1b) with a weighting scheme (e.g., a linear function) to generate a statistic known to correlate with the physiological state of fasting.

In some cases, the Low Blood Glucose Risk Estimator 212 may output $\{LBGR_d\}$ as:

a. A percentile (e.g., the $1^{st}$ percentile) of the EGV History on day d. In words, this percentile characterizes the fraction of time that the patient spends with their blood glucose below a certain level of mg/dL. For example, if the $1^{st}$ percentile of EGV History on day d is 68 mg/dL, then the patient spent 1% of day d with their blood glucose below 68 mg/dL. Their $1^{st}$-percentile LBGR is 68. A larger or smaller percentile may be chosen to modify the severity of the Low Blood Glucose Risk assessed by the algorithm.

b. Low Blood Glucose Index (LBGI), using the risk space approach described in U.S. Pat. No. 11,355,238 or U.S. Pat. No. 9,317,657.

c. Actionable low blood glucose risk value as described in U.S. Pat. Appl. No. 20200178905.

d. The left (negative) side of the Average Daily Risk Range value documented by Patton and Clements (see Patton S R, Clements M A. Average daily risk range as a measure for clinical research and routine care. J Diabetes Sci Technol. 2013 Sep. 1; 7(5):1370-5. doi: 10.1177/193229681300700529. PMID: 24124966; PMCID: PMC3876383).

In some cases, the Time Below 70 Identifier 214 may output $\{I_{<70,d}\}$ as:

a. True for any day d in which several (e.g., 3) consecutive elements of EGV History are below 70 mg/dL. False for all other days.

b. Alternatively, $I_{<70,d}$ could be computed as an indicator of some other quantitative assessment of exposure to non-severe hypoglycemia.

In some cases, the Time Below 54 Identifier 216 may output $\{I_{<54,d}\}$ as:

a. True for any day d in which several (e.g., 3) consecutive elements of EGV History are below 54 mg/dL. False for all other days.

b. Alternatively, $I_{<54,d}$ could be computed as an indicator of some other quantitative assessment of exposure to non-severe hypoglycemia.

In some cases, the Reference Blood Glucose Calculator 218 may output $BG_{ref}$ as:

a. The value of $EFBG_d$ on the day d for which $BG_{ref}$ is to be rendered. This alternative would drive the Adjusted Dose toward one that achieves a specified target fasting blood glucose.

b. The value of $LBGR_d$ on the day d for which $BG_{ref}$ is to be rendered. This alternative would drive the Adjusted Dose toward one that achieves a specified Low Blood Glucose Risk.

Insulin Module

Figures 3, 4:
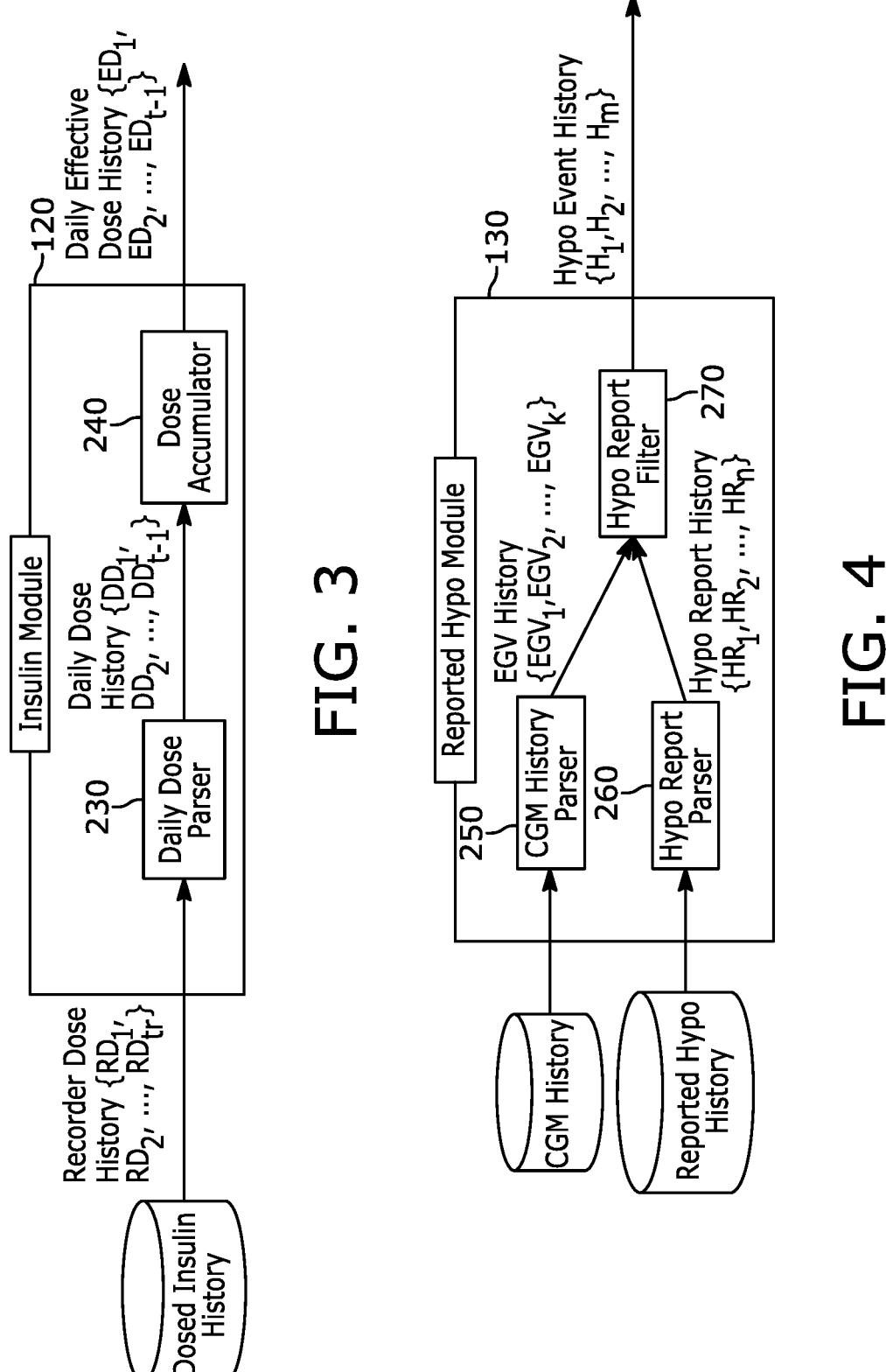
FIG. 3 shows one example of the Insulin Module shown in FIG. 1.
FIG. 4 show one example of the Reported Hypo Module shown in FIG. 1.

As illustrated in FIG. 3, the Insulin Module 120 receives or reads in the Recorded Dose History during the titration process and then renders a sequence of Daily Effective Dose History values that account for the pharmacokinetic accumulation of available insulin in blood plasma over time. The Daily Effective Dose History is used subsequently as independent variables in the effective dose-response produced by the Dose-EFBG Modeler and the Dose-LBGR Modeler.

The Insulin Module 120 performs two main steps. First, a Daily Dose Parser 230 interprets the Recorded Dose History $\{RD_1, RD_2, \ldots, RD_{tr}\}$ and produces a Daily Dose History $\{DD_1, DD_2, \ldots, DD_{t-1}\}$, as illustrated in FIG. 3. Here, each element of Recorded Dose history $RD_r$ (for r=1, 2, . . . , tr) is the r-th recorded (long-acting) insulin dose, described by both a recorded dose value and timestamp. For the Daily Dose History, each element at a specific timestamp is associated to an abstract titration day, such that $DD_d$ (for d=1, 2, . . . , t−1) is the historical total basal dose received on the d-th day of the titration process and where t−1 refers to the most recent injection prior to the one that the system is about to recommend.

Next, a Dose Accumulator 240 processes the Daily Dose History to produce an associated Daily Effective Dose History $\{ED_1, ED_2, \ldots, ED_{t-1}\}$, where $ED_d$ (for d=1, 2, . . . , t−1) is the effective dose for the patient on the d-th day of titration representing the total available (effective) plasma insulin serving the patient on that day. The effective dose (i) accounts for accumulation of insulin in the patient's body from all previously administered doses, (ii) applies to long-acting insulin with pharmacokinetic profiles measured in days (from half a day to 30 days), (iii) is used for the purpose of quantifying the relative effect of past insulin doses on a specific time window (e.g., once a day), and (iv) it can be used for various patient-specific dose-response models.

Some alternative implementations of the Insulin Module 120 are described below.

In some cases the elements of the Recorded Dose History may be collected via a "Connected" or "smart" insulin pen, user reported boluses through an "app," or an insulin injection detection algorithm (e.g. CGM based, or any combination of devices).

The time window over which the dosed insulin history may be obtained may vary. For instance, it may a time window of 12 hours in the case of 2 injections per day, a time window of 1 day for daily injections (as described in the example above), or a time window of 1 week for weekly injections.

The total basal dose may be calculated by the Daily Dose Parser 230 as the result of a single injection of basal (long-acting) insulin on day d, as the sum of multiple doses on day d, or as the weighted sum of multiple doses on day d (weighted with a time degradation coefficient—such that the further in past the dose was injected the lower the weight).

In some cases the computation of the effective dose may be based on a linear model of the effect of daily doses on day d from the last N days, derived from a PK/PD model, derived from patient-specific or population data, or learned online or predetermined.

Reported Hypoglycemia (Hypo) Module

As illustrated in FIG. 4, the Reported Hypo Module 130 receives or otherwise reads in the CGM History and Reported Hypo History and then renders the Hypo Event History. The patient generates each record in the Reported Hypo History, and thus these records might contain certain deficiencies. For example, these records might refer to a Hypo Event in the distant past, or they might report a Hypo Event when none, in fact, occurred physiologically. The Reported Hypo Module 130 filters the Reported Hypo History down to a Hypo Event History in which each Hypo Event is both relevant and credible for the next Adjusted Dose. Hypoglycemia is a primary risk of basal insulin therapy, and these Hypo Events assist other modules of the system in mitigating adverse hypoglycemic episodes.

As shown in FIG. 4, the Reported Hypo Module 130 includes (1) a CGM History Parser 250 that reads the CGM History and produces an EGV History {EGV$_1$, EGV$_2$, ..., EGV$_k$}, (2) a Hypo Report Parser 260 that reads the Reported Hypo History and produces a Hypo Report History {HR$_1$, HR$_2$, ..., HR$_n$}, and (3) a Hypo Report Filter 270 that combines the EGV History and the Hypo Report History to render a Hypo Event History {H$_1$, H$_2$, ..., H$_m$}. Each element HR$_i$ of the Hypo Report History comprises a timestamp of the Hypo Event experience, a timestamp of the Hypo Report submission, and an indicator of the Hypo Event's severity. The elements of the Hypo Report History are ordered by timestamp of the Hypo Event and are nonduplicative with each other. The Hypo Report History is provided as input to the Hypo Report Filter 270, which determines whether each HR is sufficiently relevant and credible. All Hypo Reports that are sufficiently relevant and credible pass through the Hypo Report Filter 270 and become part of the Hypo Event History, whose length may vary from empty (i.e., no Hypo Events) to the length of the Hypo Report History (i.e., all Hypo Reports are retained as Hypo Events).

In some embodiments, the Hypo Report relevance may be found to be irrelevant. For example, the Hypo Report may be deemed irrelevant if its age (relative to the current time) is greater than a prespecified threshold (e.g., 7 days). This threshold will determine when Hypo Events lose relevance for the next Adjusted Dose. The Hypo Report may also be deemed irrelevant if the Hypo Event was experienced at a time when the Adjusted Dose was substantially different from the current Adjusted Dose. For example, if the Hypo Event was experienced when the Adjusted dose was 37 U/day, whereas the current dose is only 10 U/day, then the Hypo Report might be deemed irrelevant for the next Adjusted Dose. The Hypo Report may also be deemed irrelevant if its severity is sufficiently low.

In some embodiments, the Hypo Report may be deemed noncredible. For instance, it may be deemed noncredible if its age (relative to the current time) is greater than a prespecified threshold (e.g., 2 days). This threshold will determine when Hypo Reports lose credibility due to memory recall limitations, for example. A Hypo Report also may be deemed noncredible if the EGV History is credible and consistently above a certain threshold (e.g., 130 mg/dL) at the time of the Hypo Event, such that the Hypo Event is unlikely to be valid. For example, the patient might key in the wrong date for a Hypo Event, and the EGV History may pick out such errors.

Dose-EFBG Modeler

Figures 5, 6:
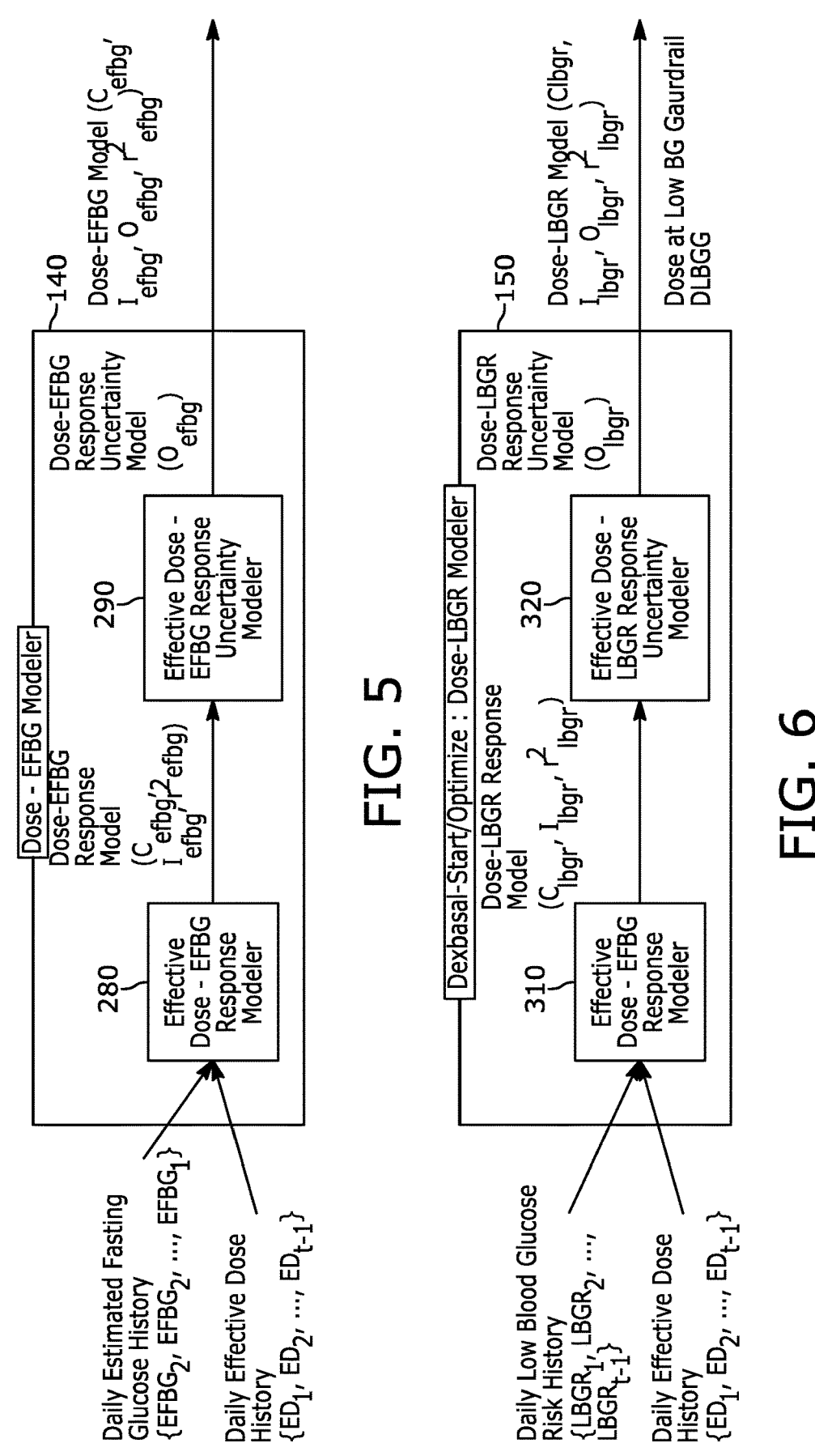
FIG. 5 shows one example of the Dose-EFBG Modeler shown in FIG. 1.
FIG. 6 shows one example of the Dose-LBGR Modeler shown in FIG. 1.

As shown in FIG. 5, the Dose-EFBG Modeler 140 receives a history of Estimated Fasting Blood Glucose values as well as a history of Effective Doses of insulin. The modeler outputs a Dose-EFBG regression model that predicts the Estimated Fasting Blood Glucose that corresponds to an Effective Dose. In addition to an Estimated Fasting Blood Glucose prediction, the Dose-EFBG model may include an assessment of how variable this prediction will be.

FIG. 5 show the inputs and outputs of the Dose-EFBG Modeler 140 produced during day t. The Dose-EFBG Modeler 140 receives two streams of inputs at day t:

1. A daily history of Estimated Fasting Blood Glucose values, labeled EFBG$_d$ for days d=2, ..., t, as generated by the CGM Module.
2. A daily history of Estimated Effective Insulin Doses, labeled ED$_d$ for day d for days d=1, 2, ..., t−1, as generated by the Insulin Module.

Based on these inputs, in one embodiment, tan Effective Dose-EFBG Response Modeler 280 produces a linear regression model with intercept I$_{efbg}$ and coefficient C$_{efbg}$ relating Estimated Fasting Blood Glucose to an Effective Dose of insulin.

To bias the regression model toward a safe population average dose response in early stages of the titration process, the linear regression objective is modified by adding a regularization term as follows:

$$I_{efbg}, C_{efbg} = \arg\min_{I,C} \sum_{d=1}^{t-1} (I + C*ED_d - EFBG_{d+1})^2 + \frac{(C-\mu_C)^2}{\sigma_C}$$

based on a normally distributed population model for coefficient C$_{efbg}$ with mean $\mu_C$ and standard deviation $\sigma_C$. The population model is based on historical observed values for C$_{efbg}$ and guides model fitting when the histories of EFBGs and EDs are too short to produce reliable regression models. The Effective Dose-EFBG Response Modeler 140 also produces an assessment of fitness r$^2_{efbg}$ of the regression model.

The Effective Dose-EFBG Response Uncertainty Modeler 290 calculates the variance of the residuals produced by the Effective Dose-EFBG Response Modeler. It also applies a constant learning rule to update its estimate of variance labeled s$_{efbg}$.

In one embodiment, the Estimated Fasting Blood Glucose is estimated from CGM data by looking at the estimated glucose value at a particular time of day (e.g., about 5:30 AM). An alternative embodiment may account for potential early meals by selecting the last CGM reading before a detected meal. In some implementations alternatives to the EFBG may be used that are more descriptive of the steady-state of the patients. These alternatives may include the median or another percentile of the patient's glucose distribution or a model of the glucose distribution.

Various embodiments of the Effective Dose-EFBG Response Modeler 280 may employ non-linear regression models, machine-learning methods, including neural-networks and may incorporate additional predictors in addition to Effective Doses. Also, the population model used in regularization can be multi-variate and include all regression model parameters. Likewise, historical CGM data may be used to produce a Digital Twin or Clone of the patient and simulate this model as an alternate method to produce an Estimated Fasting Blood Glucose value corresponding to an Effective Dose.

Various embodiments of the Effective Dose-EFBG Response Uncertainty Modeler 290 may employ a variance model that changes with the size of Effective Dose and/or a variance model that is dependent on other features.

Dose-LBGR Modeler

As shown in FIG. 6, the Dose-LBGR Modeler 150 receives a history of Low Blood Glucose Risk values as well as a history of Effective Doses of insulin. The modeler outputs a Dose-LBGR regression model that predicts the Low Blood Glucose Risk that corresponds to an Effective Dose. In addition to a Low Blood Glucose Risk prediction, the Dose-LBGR model includes an assessment of how variable this prediction will be, as well as an estimate of the insulin dose that would achieve the maximum hypoglycemia threshold, called Dose at Low BG Guardrail FIG. 6 shows the inputs and outputs produced during day t by the Dose-LBGR Modeler 150. The Dose-LBGR Modeler 150 receives two streams of inputs at day t. One input stream represents a daily history of Low Blood Glucose Risk values, labeled $LBGR_d$ for days d=1, . . . , t–1, as generated by the CGM Module. In one embodiment, Low Blood Glucose Risk is defined as the 0.5 percentile of the patient's CGM values. Another inputs stream represents a daily history of Estimated Effective Insulin Doses, labeled $ED_d$ for day d for days d=1, 2, . . . , t–1, as generated by the Insulin Module.

Based on these inputs, the Effective Dose-LBGR Response Modeler 310 produces a linear regression model with intercept $I_{lbgr}$ and coefficient $C_{lbgr}$ relating Low Blood Glucose Risk to an Effective Dose of insulin.

To bias the regression model toward a safe population average dose response in early stages of the titration process, the linear regression objective is modified by adding a regularization term as follows:

$$I_{lbgr}, C_{lbgr} = \arg \min_{I,C} \sum_{d=1}^{t-1} (I + C*ED_d - LBGR_d)^2 + \frac{(C - \mu_C)^2}{\sigma_C}$$

based on a normally distributed population model for coefficient $C_{lbgr}$ with mean $\mu_C$ and standard deviation $\sigma_C$. The population model is based on historical observed values for $C_{lbgr}$ and guides model fitting when the histories of LBGRs and EDs are too short to produce reliable regression models. The Effective Dose-LBGR Response Modeler 310 also produces an assessment of fitness $r^2_{lbgr}$ of the regression model as well as Dose at Low BG Guardrail. The latter is the maximum dose that will not result in the likelihood of hypoglycemia being larger than 5%.

The Effective Dose-LBGR Response Uncertainty Modeler 320 then calculates the variance of the residuals produced by the Effective Dose-LBGR Response Modeler 310. It also applies a constant learning rule to update its estimate of variance labeled $s_{lbgr}$.

In some cases alternative definitions of Low Blood Glucose Risk may be employed which could include a Low Blood Glucose Index (LBGI) or other percentiles.

In some alternative embodiments, the Effective Dose-LBGR Response Modeler 310 may employ non-linear regression models, machine-learning methods, including neural-networks, and/or additional predictors in addition to Effective Doses. In addition, a population model may be used in regularization that is multi-variate and includes all regression model parameters. Also, historical CGM data can be used to produce a Digital Twin or Clone of the patient and simulate this model as an alternate method to produce a Low Blood Glucose Risk value corresponding to an Effective Dose.

Alternative embodiments of the Effective Dose-LBGR Response Uncertainty Modeler 320 may employ a variance model that changes with the size of Effective Dose and/or a variance model that changes with other features.

Target Dose Adjuster

Figure 7:
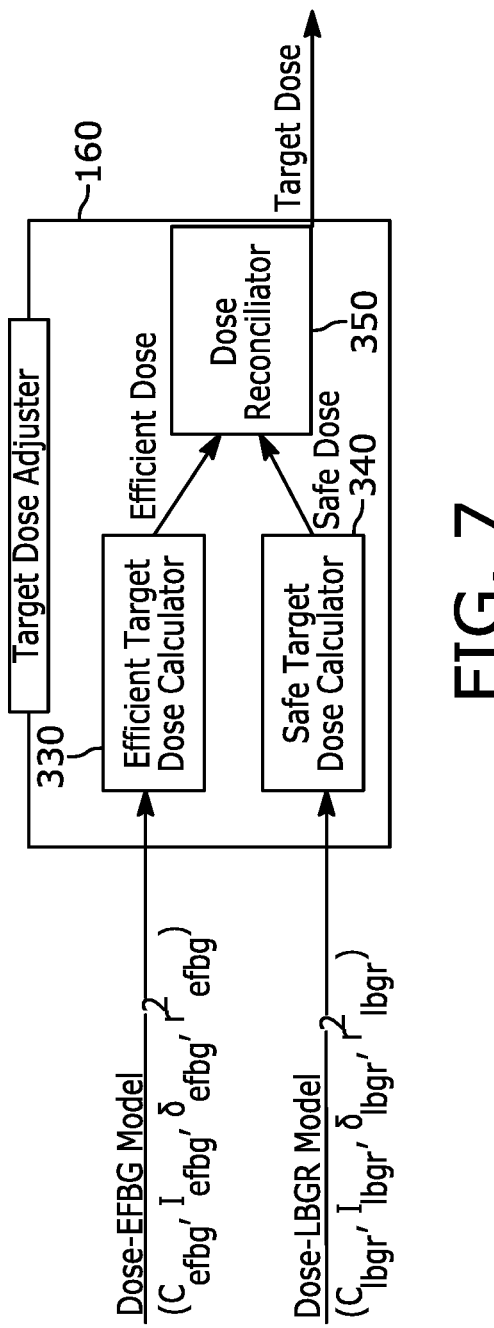
FIG. 7 shows one example of the Target Dose Adjuster shown in FIG. 1.

As shown FIG. 7, the Target Dose Adjuster 160 receives as inputs the Dose-EFBG Model from the Dose-EFBG Modeler 140 and the Dose-LBGR Model from the Dose-EFBG Modeler 150 and outputs a Target Dose resulting from a tradeoff between efficiency and safety. The Target dose is provided to the Dose Finalizer 170.

The submodules of the Target Dose Adjuster 160 performs three primary steps. The first and second described below may be performed in parallel.

In the first step, an efficient Target Dose Calculator 330 takes the Dose-EFBG Model as input and produces an Efficient Dose from an inversion of the model. The Dose-EFBG Model contains the elements necessary to (i) predict an Estimated Fasting Blood Glucose value and the error around it from a basal insulin dose (ii) assess the quality of the predictions. In one implementation of the Dose-EFBG Modeler 140, the prediction is performed with a linear model with a coefficient $C_{efbg}$ and intercept $I_{efbg}$, the error around the prediction is described as having 68% chance to fall within $s_{efbg}$ of the prediction, and the quality of the predictions is assessed with the r-square value ($r^2_{efbg}$). If the quality of the predictions is deemed too poor ($r^2_{efbg}$ to low), no Efficient Dose is produced, otherwise, the Efficient Dose is the dose that satisfies the desired Estimated Fasting Blood Glucose with a certain level of confidence (accounting for the prediction error). In one implementation, the Efficient Dose is the dose based on $s_{efbg}$. The patient's actual response is equally likely to lie above or below the target fasting blood glucose.

In the second step, a Safe Target Dose Calculator 340 takes the Dose-LBGR Model as input and produces a Safe Dose from an inversion of the model. The Dose-LBGR Model contains the elements necessary to (i) predict a Low Blood Glucose Risk value and the error around it from a basal insulin dose (ii) assess the quality of the predictions. In one implementation of Dose-LBGR Modeler 150, the prediction is done with a linear model with a coefficient $C_{lbgr}$ and intercept $I_{lbgr}$, the error around the prediction is described as having 68% chance to fall within $s_{lbgr}$ of the prediction, and the quality of the predictions is assessed with the r-square value ($r^2_{lbgr}$). If the quality of the predictions is deemed too poor ($r^2_{lbgr}$ to low), no Safe Dose is produced, otherwise, the Safe Dose is the dose that satisfies the desired Low Blood Glucose Risk with a certain level of confidence (accounting for the prediction error). In one implementation, the Safe Dose is the dose, based on $s_{lbgr}$, that yields a 95% chance that the actual LBGR response will correspond to hypoglycemia exposure below a defined threshold.

In the final step performed by the Target Dose Adjuster 160, a Dose Reconciliator 350 takes the Efficient Dose and the Safe Dose as inputs and produces a Target Dose. The Target Dose is the result of a tradeoff between the Efficient Dose and the Safe Dose. In one implementation the Target Dose is equal to the Safe Dose.

In some implementations the Target Dose Adjuster 160 may use any of the various embodiments of the Dose-EFBG Model and the Dose-LBGR Model described above. Also, the level of confidence that is used can be set to any suitable value.

Figure 8:
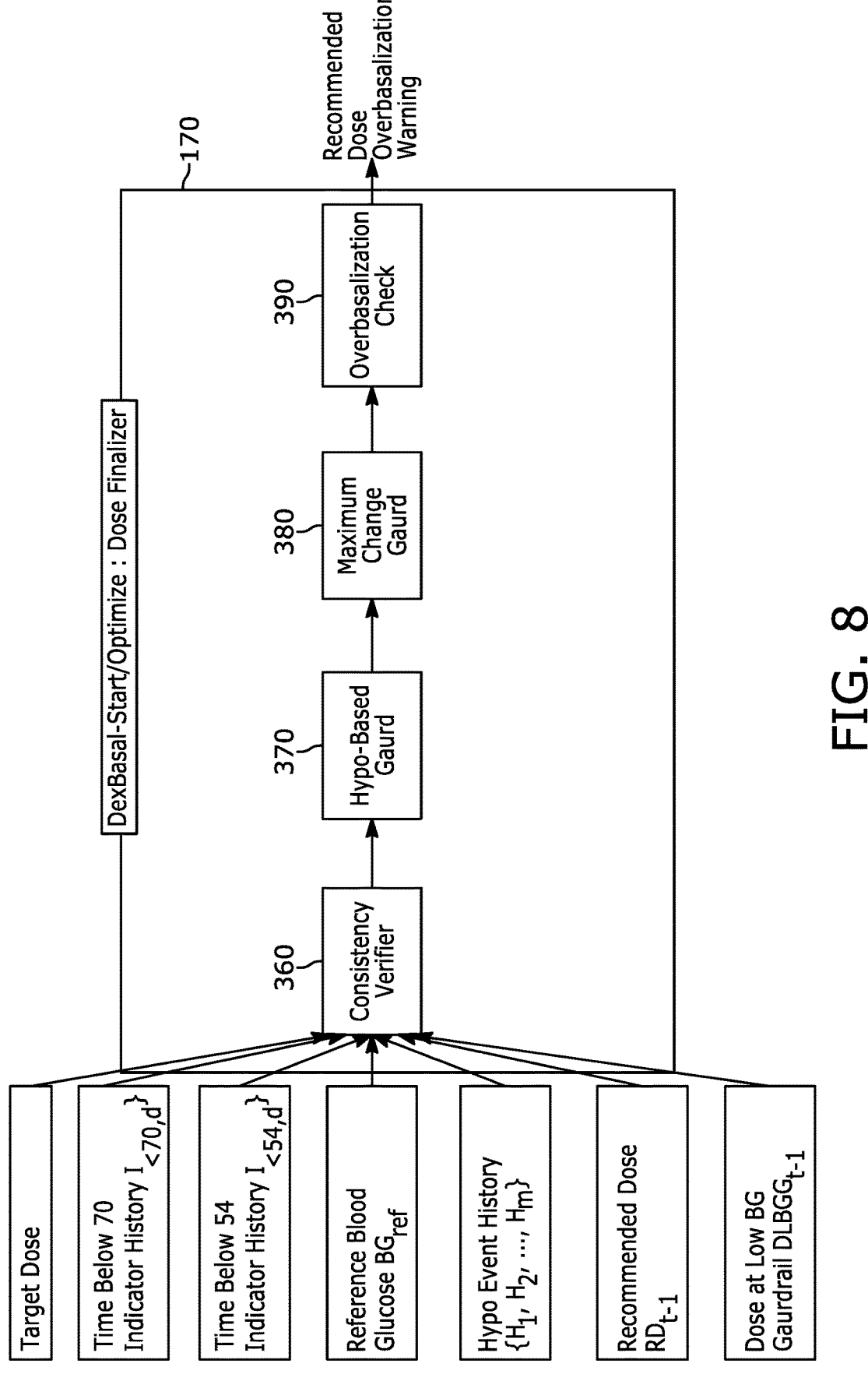
FIG. 8 shows one example of the Dose Finalizer shown in FIG. 1.

In some embodiments, the Dose Reconciliator 350 may employ a minimum of the Efficient Dose and the Safe Dose, a maximum of the Efficient Dose and the Safe Dose or a weighted average of the Efficient Dose and the Safe Dose, with weights computed from model accuracy and/or prediction error Dose Finalizer As shown in FIG. 8, inputs to the Dose Finalizer 170 include the Target Dose, outputs from the CGM Module 110 ($\{I_{<70,d}\}$, $\{I_{<54,d}\}$, and $BG_{ref}$), the Hypo Event History $\{H_1, H_2, \ldots, H_m\}$, the most recent Adjusted Dose ($RD_{t-1}$), and the Dose at Low BG Guardrail $DLBGG_{t-1}$. The module applies a set of safeguards and outputs a new Adjusted Dose.

The Dose Finalizer 170 applies a set of safeguards to a proposed Target Dose to mitigate hypoglycemia risk and prevent large dose changes with respect to the current Adjusted Dose $RD_{t-1}$. In this regard the Dose Finalizer 170 can define a Target Deadband surrounding a target glucose value, which is a design parameter of the algorithm. The Target Deadband is a range of glucose values within which the Adjusted Dose will not change. The individual submodules of the Dose Finalizer 170 operate as follows.

The Consistency Verifier 360 applies a set of rules to ensure the proposed Target Dose responds to the clinical state of the patient. For instance, it may set the Adjusted Dose to the current dose $RD_{t-1}$ if $BG_{Ref}$ is in the Target Deadband. It may also set the Adjusted Dose to the current dose $RD_{t-1}$ if $BG_{Ref}$ is below the Target Deadband and the Target Dose is greater than the current dose $RD_{t-1}$. The Consistency Verifier 360 may also Set the Adjusted Dose to a value greater than $RD_{t-1}$ if $BG_{ref}$ is above the Target Deadband.

The Hypo-Based Guard 370 will ensure that the resulting Adjusted Dose does not produce hypoglycemia e.g., 95% of the time by limiting the Adjusted Dose=min(Adjusted Dose, $DLBGG_{t-1}$). This module will further prevent any dose increases in the presence of recent indications from $\{I_{<70,d}\}$ or $\{I_{<54,d}\}$ or the Hypo Event History $\{H_1, H_2, \ldots, H_m\}$.

The Maximum Change Guard 380 guarantees a smooth change of doses by setting a Maximum Change. If the proposed Target Dose will change the current Adjusted Dose $RD_{t-1}$ by more than the Maximum Change, the maximum change is applied instead by setting Adjusted Dose=$RD_{t-1}$+ Maximum Change.

Finally, the Overbasalization Check 390 creates a warning if the Target Dose is beyond clinically acceptable limits of basal insulin therapy for the patient. This is a prediction that overbasalization may occur in the future. It also creates a warning if the Adjusted Dose produced by the Maximum Change Guard is beyond clinically acceptable limits of basal insulin therapy for the patient. This is an assertion that overbasalization is currently present.

In some alternative embodiments, the Dose Finalizer 170 may employ any of a variety of different rules for establishing maximum allowable changes. Also, in some cases the Hypo Based Guard 370 could be based on risk or other hypoglycemia related metrics. Finally, in some implementations overbasalization could introduce a constraint on the dose, as opposed to simply being a warning.

Termination Checker

Figure 9:
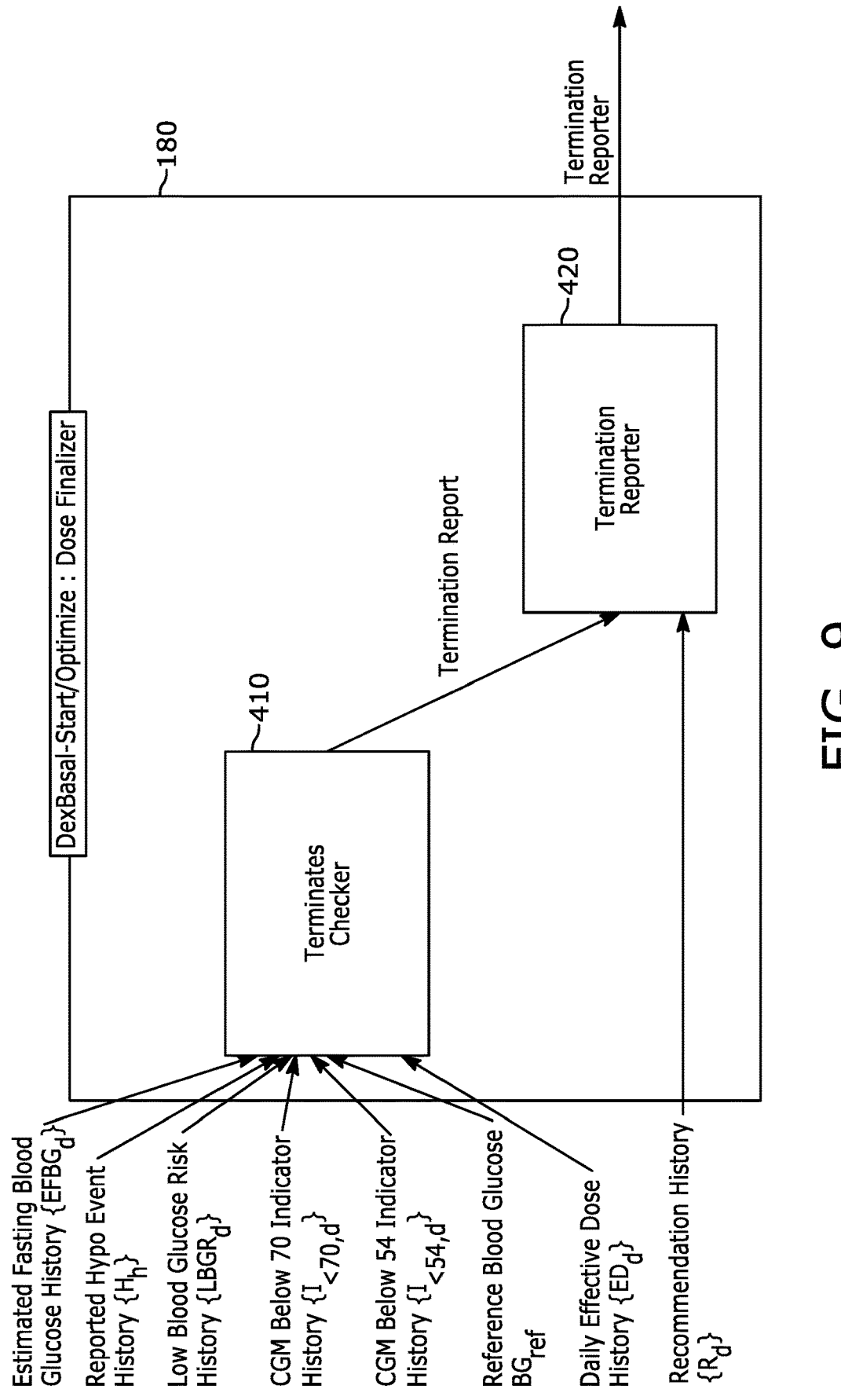
FIG. 9 shows one example of the Termination Checker shown in FIG. 1.

As shown in FIG. 9, the Termination Checker 180 includes a Termination Checker Submodule 410 that receives as inputs the Estimated Fasting Blood Glucose History, Hypo Event History, Low Blood Glucose Risk History, Time Below 70 Indicator History, Time Below 54 Indicator History, Reference Blood Glucose, Daily Effective Dose History and the Recommendation History and outputs the Termination Report. As shown in FIG. 1:

Estimated Fasting Blood Glucose History refers to the output of CGM Module

Reported Hypo Event History refers to the output of Reported Hypo Module

Low Blood Glucose Risk History refers to the output of CGM Module

CGM Below 70 Indicator History refers to the output of CGM Module

CGM Below 54 Indicator History refers to the output of CGM Module

Reference Blood Glucose $BG_{ref}$ refers to the output of CGM Module

Daily Effective Dose History refers to the output of Insulin Module

The Recommendation History that is used as an input, where each element of Recommendation History $R_d$ (for d=1, 2, . . . , t) is the recommendation element for the d-th day, is described by both an Adjusted Dose (output of Dose Finalizer) and a Termination Report (output of Termination Checker). Likewise, the termination Report that is also used as an input, contains the termination information such as if a termination took place and if yes, the timestamp and reason of the termination.

The Termination Checker 180 performs two primary steps. In the first step, the Termination Checker Submodule 410 receives all the inputs and outputs a Termination Report. In one implementation, the Termination Checker Submodule 410 checks what elements in a given list of termination criteria are verified. The Termination Report returns yes if any criteria is verified and if yes, it specifies which ones. In one particular implementation, three different criteria can terminate the titration process:

a. The seven past elements of the Estimated Fasting Blood Glucose History are all within the desired target range and the seven past elements of Time Below 70 Indicator History are all below a desired target and the seven past elements of Time Below 54 Indicator History are all below a desired target and there are no elements in the Hypo Event History with a timestamp within the past seven days.

b. The seven past Adjusted Doses obtained from the last elements of Recommendation History are equal to zero.

c. The Termination Deadline has been reached: which is a predetermined termination deadline of 30 days.

In the second primary step performed by the Termination Checker 180, the Termination Reporter 420 receives a Termination Report and Recommendation History as inputs from the Termination Checker Submodule 410. The Termination Reporter 420 returns the last Termination Report from Recommendation History if this one indicates that a termination took place and returns the Termination Report from the Termination Checker 180 otherwise.

In some alternative embodiments, the Termination Checker Submodule 410 may use different inputs. For instance, termination decisions could be based on alternative CGM or insulin dose statistics that could be computed by the CGM or Insulin Modules, respectively. The Termination Checker Submodule 410 also may use alternative glycemic or insulin metrics that more broadly reflect diabetes management criteria (e.g. time in range, estimated HbA1c).

Likewise, different embodiments may use different termination criteria on which to make termination decisions. For instance, termination decisions may be based on alternative statistics related to the patient's experience of hypoglycemia that could be computed by the Reported Hypo Module 130. Alternatively, termination decisions may be based on patient satisfaction or caregiver satisfaction. In addition, the termination criteria may use different assessment windows or any metric reaching the desired target range for any amount of time In some cases the Termination Report may be based on the system's inability to reach a target $BG_{ref}$ without exposure to hypoglycemia within a desired number of titration days. In this case the report may indicate that variability in the CGM trace, regardless of whether it is due to the patient's physiology or behavior, limits the ability to reach a target $BG_{ref}$ without also introducing prandial insulin, e.g., multiple daily injection therapy.

Figure 10:
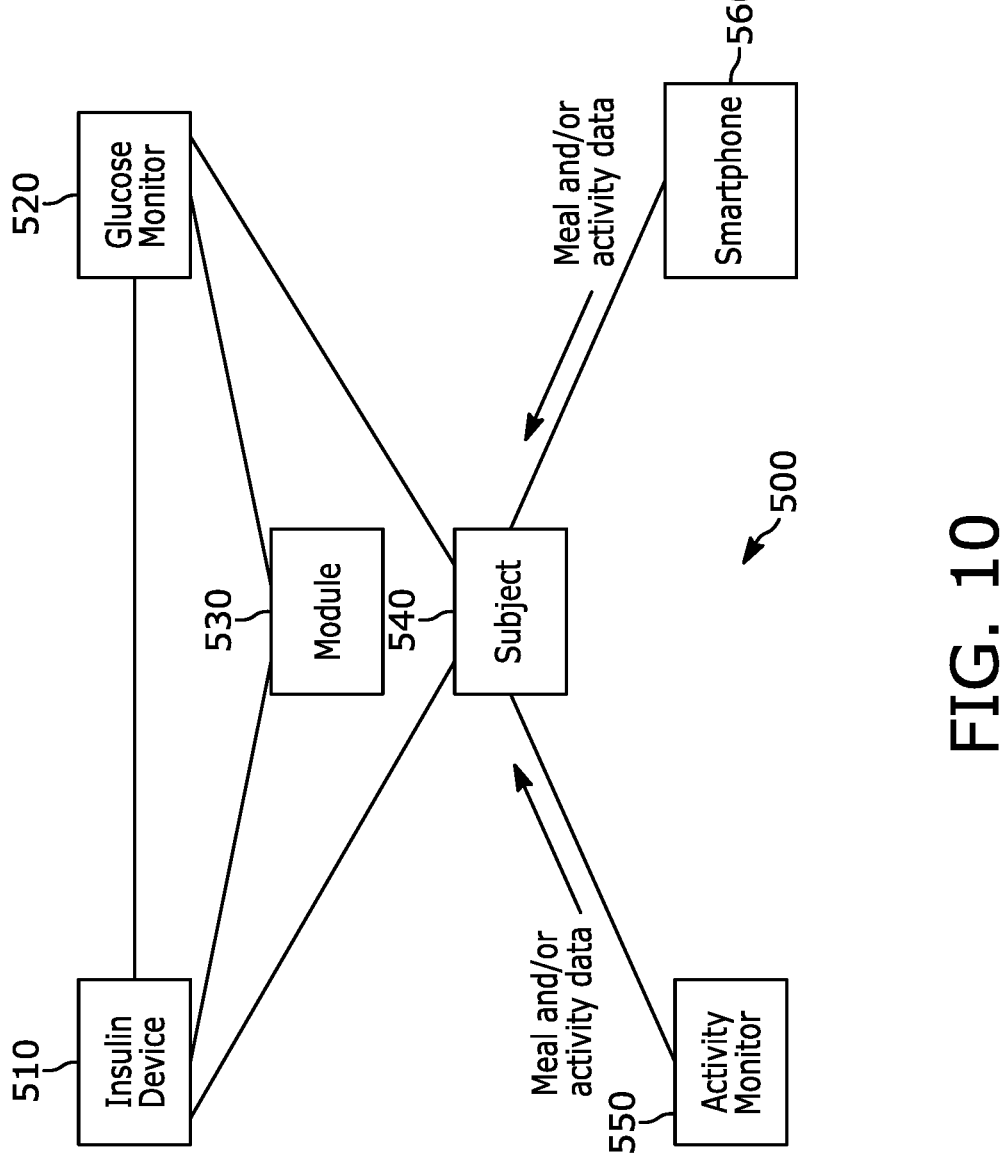
FIG. 10 shows one example of an illustrative operating environment in which the basal titration adjustment system and method described herein may operate.

FIG. 10 shows one example of an illustrative operating environment in which the basal titration adjustment system and method described herein may operate. Of course, those of ordinary skill in the art will recognize that the basal insulin titration adjustment system and method may be used in other environments as well and in some cases may even operate as an independent device or, alternatively, the method may be implemented on any suitable computing device that incorporates additional functionality. As shown, the environment comprises an insulin delivery device 110, a glucose monitor 120, a processor 130, a subject 140, an activity monitor 150, and a smartphone 160.

One or more of the insulin delivery device 110, the glucose monitor 120, the processor 130, the activity monitor 150, and the smartphone 160 may be in communication through a network. The network may be a variety of network types including the public switched telephone network (PSTN), a cellular telephone network, and a packet switched network (e.g., the Internet). Although only insulin delivery device 110, one glucose monitor 120, one processor 130, one subject 140, one activity monitor 150, and one smartphone 160 are shown in FIG. 1, there is no limit to the number of insulin delivery devices 110, glucose monitors 120, processors 130, subjects 140, activity monitors 150, and smartphones 160 that may be supported.

The insulin delivery device 110 may be any device that dispenses insulin, such as syringes, pumps (e.g., external, mechanical, patch, or implanted), and inhalers, for example. The insulin delivery device 110 may also include devices that dispense other drugs that help control glucose levels like glucagon (dual-hormone artificial pancreas), GLP-1, etc. Depending on the particular type of device employed, the insulin delivery device may or may not be a connected device that is in communication through a network.

The glucose monitor 120 may be any type of CGM or SMBG (self-monitoring of blood glucose) device, depending on the implementation. The glucose monitor 120 may be a connected device that provides glucose readings continuously or provides a set of glucose readings when the device is scanned or downloaded. In addition to glucose readings, the glucose monitor 120 may record user interactions such as when and how a user (e.g., a subject, a patient, a caregiver, a medical professional, etc.) views their glucose traces and how they respond to alerts and alarms. The user interaction can provide insights into the timing and motivation of treatment decisions including why and when they are considering the effects of eating or dosing insulin.

Figure 11:
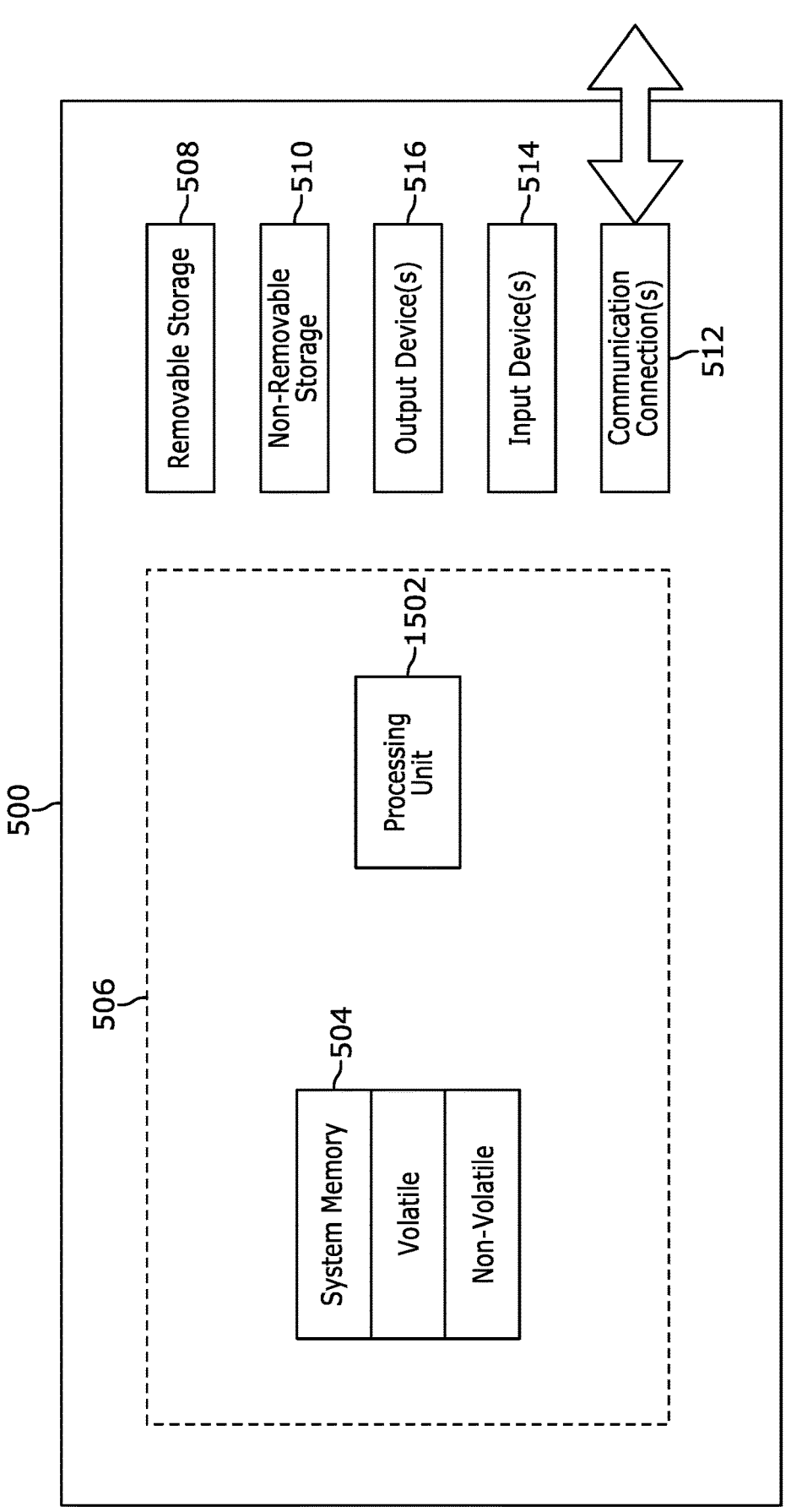
FIG. 11 shows one example of a computing device in which example embodiments and aspects may be implemented.

The processor 130 collects data from the insulin delivery device 110 and the glucose monitor 120 and the subject 140 and, in some embodiments, may run the basal insulin titration methods described herein. The processor 130 (as well as the insulin delivery device 110, the glucose monitor 120, the activity monitor 150, and/or the smartphone 160) may be implemented using a variety of computing devices such as smartphones, desktop computers, laptop computers, and tablets, for example. In this regard the processor 130 may a processor that is available in one of the other devices shown in the operating environment of FIG. 1, such as the smartphone 160, the activity monitor 150 or, depending on the type employed (e.g., a smart pen), the insulin device 110. Other types of computing devices in which the processor 130 may be incorporated also may be supported. A suitable computing device is illustrated in FIG. 11 as the computing device 500.

To provide a robust system, the calculations performed by the processor 130 may be dynamic and distributed depending on which devices and processors are connected. For example, cloud computing may be used when there is connectivity, a smartphone processor may be used when there is no connectivity and then a transmitter or a smartwatch may be used when the smartphone is not connected. Complex calculations, like model optimization, may only run when more powerful processors are available. When powerful processors are not available, algorithms may use the most recent parameters or simpler approximations.

The subject 140 can provide inputs to the system including information about meals, activity, and diabetes treatments (e.g., basal insulin injections) using, for instance, any computing device that is in communication with the system, such as the smartphone 160 or other computing device of the subject 140. These inputs can be user-initiated or prompted by the system. These inputs can describe current, previous, and/or upcoming events.

The activity monitor 150 may be any device that monitors the user's physiologic and mental state. One example is a fitness tracker that monitors activity, exercise, and sleep with accelerometers, gyroscopes, heart rate, and oxygen sensors. This can also include smartphones as they can detect location and user activity/interactions, or a smart home device (e.g., Amazon Alexa) in some implementations, the activity monitor 150 may include devices that detect meals.

The smartphone 160 can be used as an activity and context monitor, data entry device, data collection (talking to devices with Bluetooth, NFC, Wi-Fi, etc.) and run applications (e.g., apps) that estimate nutritional information through manual entry or automated entry (e.g., photos), FIG. 11 shows an exemplary computing device in which example embodiments and aspects may be implemented. The computing device is only one example of a suitable computing device and is not intended to suggest any limitation as to the scope of use or functionality. Numerous other general purpose or special purpose computing, devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 11, an exemplary system for implementing aspects described herein includes a computing device, such as computing device 500. In its most basic configuration, computing device 1500 typically includes at least one processing unit 502 and memory 504. Depending on the exact configuration and type of computing device, memory 504 may be volatile (such as random access memory (RAM)), non-volatile (such as read-only memory (ROM), flash memory, etc.), or some combination of the two. This most basic configuration is illustrated in FIG. 11 by dashed line 506.

Computing device 500 may have additional features/functionality. For example, computing device 500 may include additional storage (removable and/or non-removable) including, but not limited to, magnetic or optical disks or tape. Such additional storage is illustrated in FIG. 11 by removable storage 508 and non-removable storage 510.

Computing device 500 typically includes a variety of computer readable media. Computer readable media can be any available media that can be accessed by the device 500 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 504, removable storage 508, and non-removable storage 510 are all examples of computer storage media. Computer storage media include, but are not limited to, RAM, ROM, electrically erasable program read-only memory (EEPROM), flash memory or other memory technology, CD-ROM, digital versatile disks (DV)) or other optical storage, magnetic cassettes, magnetic tape, magnetic disk storage or other magnetic storage devices, or any other medium which can be used to store the desired information and which can be accessed by computing device 500. Any such computer storage media may be part of computing device 500.

Computing device 500 may contain communication connection(s) 512 that allow the device to communicate with other devices. Computing device 500 may also have input device(s) 514 such as a keyboard, mouse, pen, voice input device, touch input device, etc. Output device(s) 516 such as a display, speakers, printer, etc. may also be included. All these devices are well known in the art and need not be discussed at length here.

It should be understood that the various techniques described herein may be implemented in connection with hardware components or software components or, where appropriate, with a combination of both Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and system of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A basal titration adjustment device for titrating a basal insulin dose for a subject, comprising:

one or more processors;

a continuous glucose monitor (CGM) module that, when executed by the one or more processors, receives CGM data obtained over at least a series of days and generates historical estimated glucose values (EGVs) therefrom and further generates from the EGVs values for each of a plurality of daily blood glucose state parameters each reflective of an aspect of a blood glucose state of the subject;

an insulin module that, when executed by the one or more processors, receives daily basal insulin dose values administered to the subject over the series of days and generates therefrom daily effective doses that each represent a total plasma insulin serving the subject for that respective day and account for an accumulation of insulin in the subject from all previously administered doses;

at least a first dose-daily blood glucose state response modeler that, when executed by the one or more processors, receives a first of the plurality of daily blood glucose state parameters and the daily effective doses and generates therefrom a first regularized dose-response model relating the first daily blood glucose state parameter to an effective basal insulin dose;

a target dose adjuster that, when executed by the one or more processors, receives the first regularized dose-response model and generates therefrom a target basal insulin dose that is to produce a value of the first daily blood glucose state parameter that is predicted by the first regularized dose-response model with at least a specified confidence level; and a dose finalizer that, when executed by the one or more processors, receives the target basal insulin dose and values of one or more of the daily blood glucose state parameters and produces therefrom an adjusted basal insulin dose that modifies the target basal insulin dose in conformance with one or more pre-established safety rules.

2. The basal titration adjustment device of claim 1, wherein the plurality of daily blood glucose state parameters are selected from the group consisting of an effective fasting blood glucose (EFBG) parameter, a low blood glucose risk parameter representing a daily risk of experiencing a low EGV, a low daily EGV parameter specifying whether or not the subject experienced an EGV below a specified level on a given day and a daily reference blood glucose parameter reflecting a comparison of a daily EGV to a therapeutic target EGV.

3. The basal titration adjustment device of claim 1, wherein the plurality of daily blood glucose state parameters includes an effective fasting blood glucose (EFBG) parameter, a low blood glucose risk parameter representing a daily risk of experiencing a low EGV, a low daily EGV parameter specifying whether or not the subject experienced an EGV below a specified level on a given day and a daily reference blood glucose parameter reflecting a comparison of a daily EGV to a therapeutic target EGV.

4. The basal titration adjustment device of claim 1, wherein the first regularized dose-response model is a regularized linear regression model.

5. The basal titration adjustment device of claim 1, wherein the first regularized dose-response model is regularized using population data to bias at least an initial target dose to a safe dose at a population level.

6. The basal titration adjustment device of claim 1, wherein the first daily blood glucose state parameter is a daily estimated fasting blood glucose (EFBG) parameter.

7. The basal titration adjustment device of claim 1, wherein the first daily blood glucose state parameter is a low blood glucose risk parameter.

8. The basal titration adjustment device of claim 1, wherein the one or more pre-established safety rules reduce a risk of hypoglycemia.

9. The basal titration adjustment device of claim 1, further comprising a reported hypoglycemia module that, when executed by the one or more processors, receives hypoglycemic event data reported by the subject and generates a hypoglycemic report history from the hypoglycemic event data and the historical EGVs, the hypoglycemic report history specifying a time and severity of credible hypoglycemic events reported by the subject, wherein the dose finalizer, when executed by the one or more processors, produces the adjusted basal insulin dose using the hypoglycemic report history as an additional input.

10. The basal titration adjustment device of claim 9, further comprising a termination checker module that, when executed by the one or more processors, receives values of some or all of the plurality of daily blood glucose state parameters, the hypoglycemic report history and adjusted basal insulin doses produced on previous days and generates therefrom a termination report indicating whether titration of basal insulin should terminate or continue.

11. The basal titration adjustment device of claim 1, wherein the at least a first dose-daily blood glucose state response modeler includes a second dose-daily blood glucose state response modeler that, when executed by the one or more processors, receives a second of the plurality of daily blood glucose state parameters and the daily effective doses and generates therefrom a second regularized dose-response model relating the second daily blood glucose state parameter to an effective basal insulin dose, the target dose adjuster, when executed by the one or more processors, receives the first and second regularized dose-response models and generates therefrom the target basal insulin dose.

12. The basal titration adjustment device of claim 11, wherein the first daily blood glucose state parameter is a daily estimated fasting blood glucose parameter and the second daily blood glucose state parameter is a low blood glucose risk parameter specifying a risk that the subject has an EGV below a threshold at one or more times during a day.

13. The basal titration adjustment device of claim 4, wherein the first regularized linear-regression model includes values for a slope, intercept and a measure of uncertainty.

14. The basal titration adjustment device of claim 6, wherein values of the EFBG parameter are based on CGM data obtained at a specified time of day.

15. The basal titration adjustment device of claim 6, wherein values of the EFBG parameter are based on CGM values that are below a certain percentile of a blood glucose distribution of the subject.

16. The basal titration adjustment device of claim 9, wherein a hypoglycemic event is treated as not relevant if it occurred more than a specified period of time before a current time or if it occurred when a then-current adjusted basal insulin dose is different from a current adjusted basal insulin dose by more than a specified amount.

17. The basal titration adjustment device of claim 7, wherein the first dose-daily blood glucose state response modeler produces a basal insulin dose-low blood glucose risk regression model that predicts a low blood glucose risk corresponding to an effective basal insulin dose.

18. The basal titration adjustment device of claim 17, wherein the basal insulin dose-low blood glucose risk regression model is a linear regularized linear regression model.

19. The basal titration adjustment device of claim 18, wherein the linear regularized linear regression model is regularized using population data to bias at least an initial target dose to a safe dose at a population level.

20. The basal titration adjustment device of claim 7, wherein the low blood glucose risk parameter represents a risk that the subject has an EGV below a threshold at one or more times during a day.

21. The basal titration adjustment device of claim 7, wherein the low blood glucose risk parameter represents a daily EGV that is below a specified percentile of all EGVs for the subject during a day.

22. The basal titration adjustment device of claim 1, wherein the dose finalizer, when executed by the one or more processors, produces the adjusted basal insulin dose on a periodic basis.

23. The basal titration adjustment device of claim 22, wherein the periodic basis is a daily basis.

24. The basal titration adjustment device of claim 11, wherein the target dose adjuster, when executed by the one or more processors, determines a first preliminary target dose from the first regularized dose-response model and a second preliminary target dose from the second regularized dose-response model and produces the target dose by balancing the first preliminary target dose with the second preliminary target dose.

25. The basal titration adjustment device of claim 24, wherein the target dose that is produced is a minimum of the first and second preliminary target doses, a maximum of the first and second preliminary target doses, or a weighted average of the first and second preliminary target doses.

26. The basal titration adjustment device of claim 1, wherein the one or more preestablished safety rules prevent a value of a newly generated adjusted basal insulin dose from exceeding a previously generated adjusted basal insulin dose for a previous day.

27. The basal titration adjustment device of claim 1, wherein the one or more preestablished safety rules establish a value for a design parameter defining a target deadband of EGVs surrounding a target EGV such that a newly generated adjusted basal insulin dose will not be adjusted from a previously generated adjusted basal insulin dose for a value of a daily reference blood glucose parameter within the target deadband.

28. The basal titration adjustment device of claim 1, wherein the one or more preestablished safety rules generates a warning that overbasalization is predicted to occur.

29. The basal titration adjustment device of claim 1, wherein the one or more preestablished safety rules constrains modification of the target basal insulin dose if overbasalization is predicted to occur.

30. The basal titration adjustment device of claim 10, wherein the termination report indicates that titration of the basal insulin dose should terminate if a target value for a daily reference blood glucose parameter cannot be reached without introducing prandial insulin, the daily reference blood glucose parameter reflecting a comparison of a daily EGV to a therapeutic target EGV.

31. A method for titrating a basal insulin dose for a subject, comprising:

receiving CGM data obtained over at least a series of days and generating historical estimated glucose values (EGVs) therefrom;

generating from the EGVs values for each of a plurality of blood glucose state parameters each reflective of an aspect of a blood glucose state of the subject;

receiving basal insulin dose values administered to the subject over the series of days and generates therefrom effective doses that each represent a total plasma insulin serving the subject for that respective day and account for an accumulation of insulin in the subject from all previously administered doses;

receiving a first of the plurality of blood glucose state parameters and the effective doses and generating therefrom a first regularized dose-response model relating the first blood glucose state parameter to an effective basal insulin dose;

receiving the first regularized dose-response model and generating therefrom a target basal insulin dose that is to produce a value of the first blood glucose state parameter that is predicted by the first regularized dose-response model with at least a specified confidence level; and receiving the target basal insulin dose and values of one or more of the plurality of blood glucose state parameters and producing therefrom an adjusted basal insulin dose that modifies the target basal insulin dose in conformance with one or more pre-established safety rules.

32. The method of claim 31, wherein the basal insulin doses are administered on a daily basis.

33. The method of claim 31, wherein an adjusted basal insulin dose is produced on a daily basis.

34. A non-transitory computer-readable medium, comprising instructions for causing a computing device to perform a method, the method comprising the method of claim 31.

* * * * *